(12) United States Patent
Schaffer et al.

(10) Patent No.: US 12,214,348 B2
(45) Date of Patent: *Feb. 4, 2025

(54) MICROFLUIDIC SYSTEMS FOR MULTIPLE BIOREACTORS AND APPLICATIONS OF SAME

(71) Applicant: VANDERBILT UNIVERSITY, Nashville, TN (US)

(72) Inventors: David K. Schaffer, Nashville, TN (US); Ronald S. Reiserer, Nashville, TN (US); Michael D. Geuy, State College, PA (US); John P. Wikswo, Brentwood, TN (US)

(73) Assignee: VANDERBILT UNIVERSITY, Nashville, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/015,749

(22) PCT Filed: Jul. 19, 2021

(86) PCT No.: PCT/US2021/042141
§ 371 (c)(1),
(2) Date: Jan. 12, 2023

(87) PCT Pub. No.: WO2022/016136
PCT Pub. Date: Jan. 20, 2022

(65) Prior Publication Data
US 2023/0271181 A1 Aug. 31, 2023

Related U.S. Application Data

(63) Continuation-in-part of application No. PCT/US2020/040061, filed on Jun. 29, 2020, and a
(Continued)

(51) Int. Cl.
*B01L 3/00* (2006.01)
*F04B 43/06* (2006.01)
(Continued)

(52) U.S. Cl.
CPC ... *B01L 3/502715* (2013.01); *B01L 3/502738* (2013.01); *B01L 2300/123* (2013.01);
(Continued)

(58) Field of Classification Search
CPC .................. B01L 2400/0481; B01L 3/502738
(Continued)

(56) References Cited

U.S. PATENT DOCUMENTS

| 6,079,313 A | 6/2000 | Wolcott et al. |
| 9,618,129 B2 | 4/2017 | Block, III et al. |

(Continued)

FOREIGN PATENT DOCUMENTS

WO 2020041342 A2 2/2020

OTHER PUBLICATIONS

Esch, M B, et al., How multi-organ microdevices can help foster drug development. Adv. Drug Del. Rev., 69:158-169. 2014.
(Continued)

*Primary Examiner* — Natalia Levkovich
(74) *Attorney, Agent, or Firm* — Locke Lord LLP; Tim Tingkang Xia, Esq.

(57) ABSTRACT

A fluidic device includes a fluidic chip having a fluidic network comprising a plurality of fluidic channels in fluidic communication with a plurality of input ports, at least one output port, and at least one sensing port; and an actuator configured to engage with the fluidic network to control each fluidic channel to switch between an open state in which fluidic flow through said fluidic channel is permitted and a closed state in which no fluidic flow through said fluidic channel is permitted, so as to selectively collect fluid from
(Continued)

multiple inputs via the plurality of input ports, and direct either all of the multiple inputs to the at least one output port, or all but a single selected input to the at least one output port and the single selected input to the at least one sensing port to which an analytical instrument is operably connected.

27 Claims, 14 Drawing Sheets

Related U.S. Application Data continuation-in-part of application No. 17/269,349, filed as application No. PCT/US2019/047307 on Aug. 20, 2019, now Pat. No. 11,465,144, said application No. PCT/US2021/042141 is a continuation-in-part of application No. 17/269,329, filed as application No. PCT/US2019/047190 on Aug. 20, 2019, now abandoned.

(60) Provisional application No. 63/053,388, filed on Jul. 17, 2020, provisional application No. 62/868,303, filed on Jun. 28, 2019, provisional application No. 62/719,868, filed on Aug. 20, 2018.

(51) Int. Cl.
  *F04B 43/14* (2006.01)
  *F16K 99/00* (2006.01)

(52) U.S. Cl.
  CPC ....... *B01L 2400/0481* (2013.01); *F04B 43/06* (2013.01); *F04B 43/14* (2013.01); *F16K 99/0057* (2013.01); *F16K 2099/0084* (2013.01)

(58) Field of Classification Search
  USPC ....................................................... 422/505
  See application file for complete search history.

(56) References Cited

U.S. PATENT DOCUMENTS

| | | | |
|---|---|---|---|
| 9,874,285 B2 | 1/2018 | Block, III et al. | |
| 10,023,832 B2 | 7/2018 | Wikswo et al. | |
| 10,052,631 B2 | 8/2018 | Ben-Yakar et al. | |
| 10,078,075 B2 | 9/2018 | Wikswo et al. | |
| 10,444,223 B2 | 10/2019 | Wikswo et al. | |
| 10,464,064 B1 | 11/2019 | Wikswo et al. | |
| 10,487,819 B2 | 11/2019 | Gould et al. | |
| 10,532,354 B2 | 1/2020 | Wikswo et al. | |
| 10,538,726 B2 | 1/2020 | Wikswo et al. | |
| 2003/0008308 A1* | 1/2003 | Enzelberger | B01F 33/30 435/6.19 |
| 2015/0308578 A1* | 10/2015 | Block, III | C12M 21/08 137/625.48 |
| 2017/0056881 A1 | 3/2017 | Schultz et al. | |
| 2017/0184490 A1 | 6/2017 | Marshall et al. | |
| 2019/0064144 A1 | 2/2019 | Wikswo et al. | |

OTHER PUBLICATIONS

Abaci, H E, and Shuler, M L. Human-on-a-chip design strategies and principles for physiologically based pharmacokinetics/pharmacodynamics modeling. Integr. Biol., 7:383-391. 2015.

Wang, Y I, et al., Self-contained, low-cost Body-on-a-Chip systems for drug development. Exp. Biol. Med.:Accepted. 2017.

Maschmeyer, I, et al., A four-organ-chip for interconnected long-term co-culture of human intestine, liver, skin and kidney equivalents. Lab Chip, 15:2688-2699. 2015.

Edington, C D, et al., Interconnected Microphysiological Systems for Quantitative Biology and Pharmacology Studies. Sci. Rep., 8: 4530. 2018.

Wikswo, J P, et al., Scaling and systems biology for integrating multiple organs-on-a-chip. Lab Chip, 13:3496-3511. 2013.

Darby, S, et al., A metering rotary nanopump for microfluidic systems. Lab Chip, 10:3218-3226. 2010. PMCID: PMC4156019.

Wikswo, J P, et al., Engineering Challenges for Instrumenting and Controlling Integrated Organ-on-Chip Systems. IEEE Trans. Biomed. Eng., 60:682-690. 2013. PMCID: PMC3696887.

Markov, D A, Manuel, S, Shor, L, Opalenik, S R, Wikswo, J P, and Samson, P C. Tape underlayment rotary-node (TURN) valves for simple on-chip microfluidic flow control. Biomed. Microdevices, 12:135-144. 2010.

LeDuc, P R, Messner, W C, and Wikswo, J P. How do control-based approaches enter into biology? Annu. Rev. Biomed. Eng., 13:369-396. 2011.

Cyr, K J, Avaldi, O M, and Wikswo, J P. Circadian hormone control in a human-on-a-chip: In vitro biology's ignored component? Exp. Biol. Med., 242:1714-1731. 2017. PMCID: PMC5832251.

NCATS Supports Award-Winning Technology for Drug Development: NIH; 2018 [updated Sep. 21, 2018.

* cited by examiner

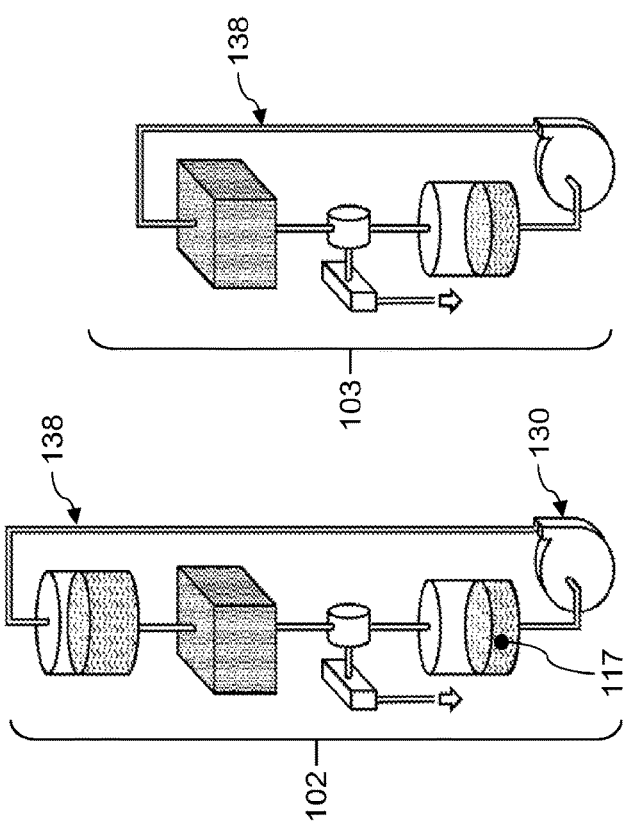
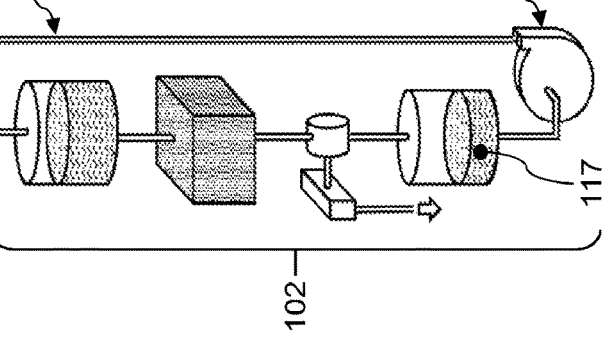
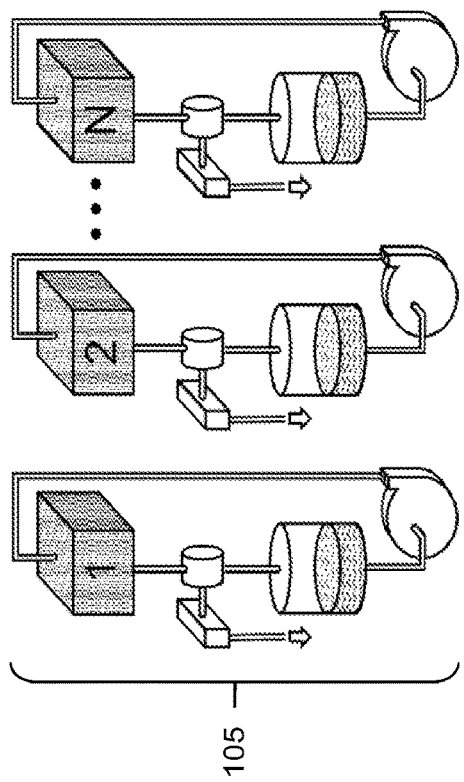
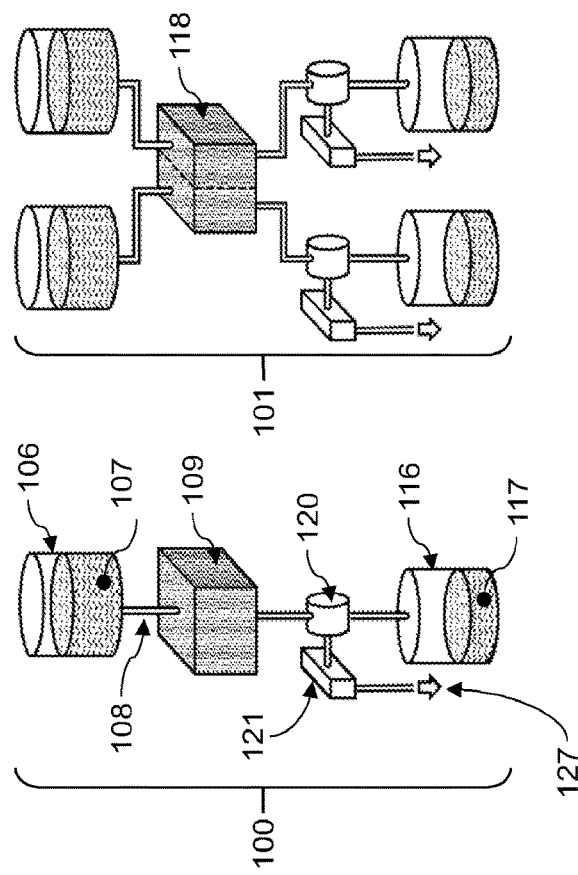
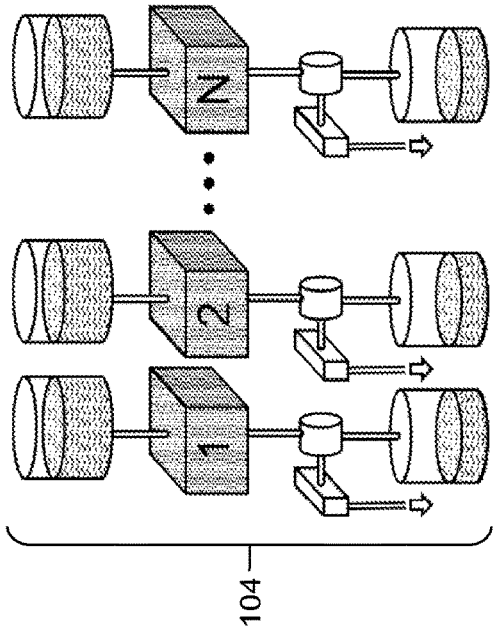

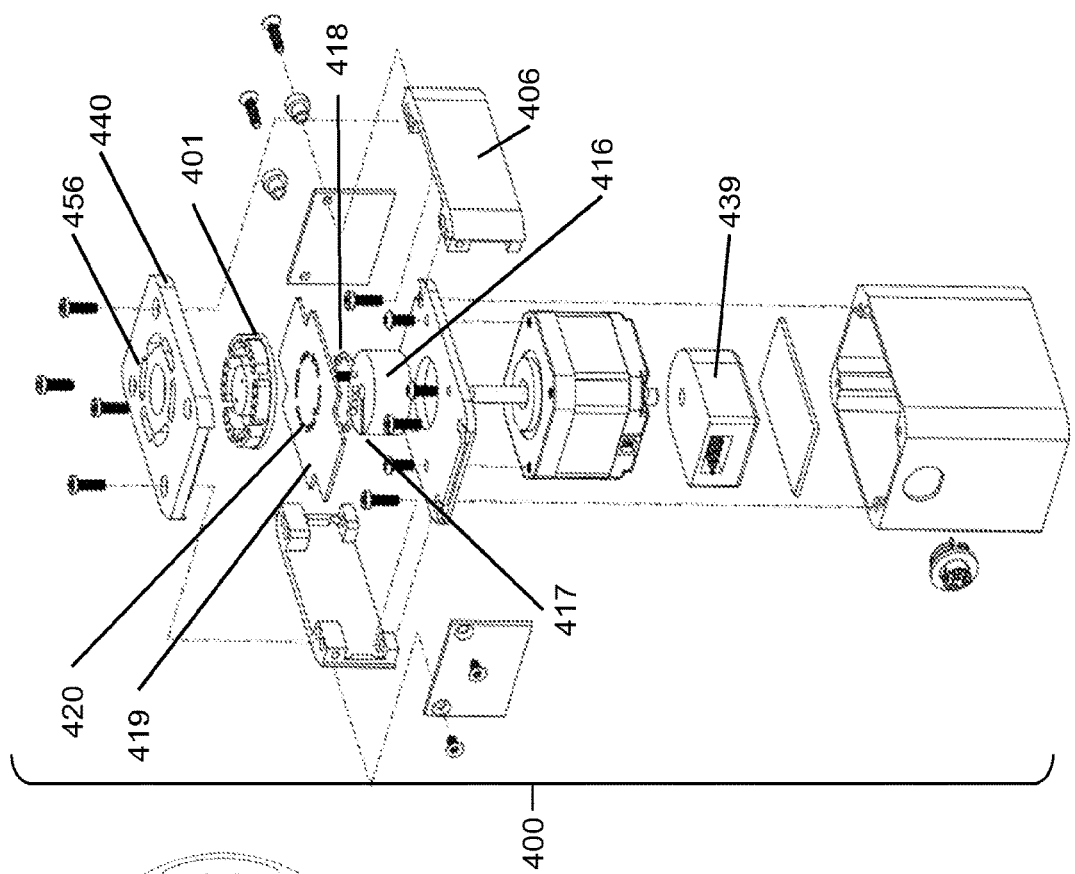
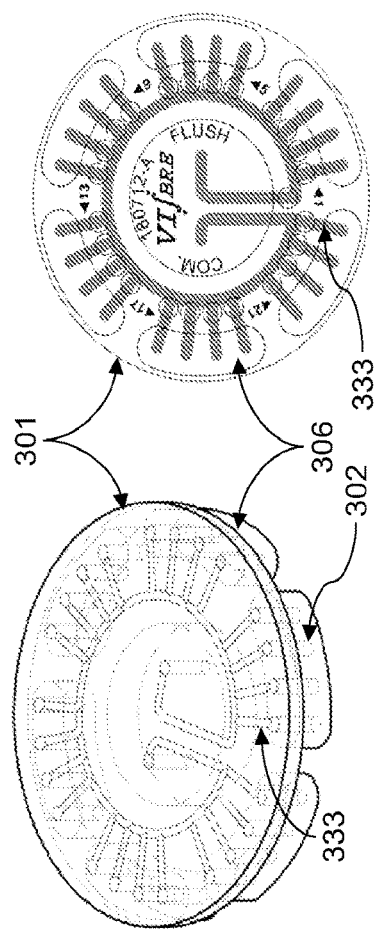
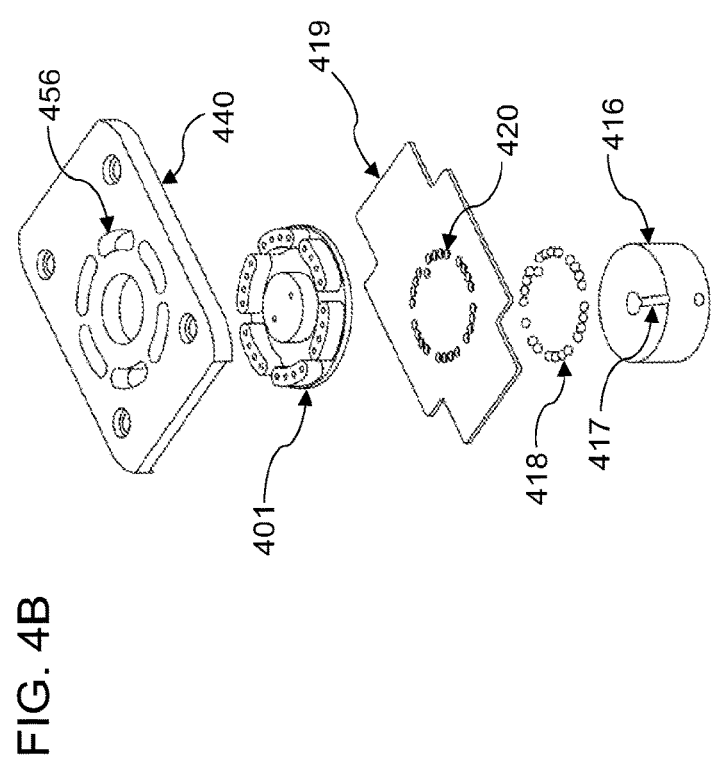
FIG. 3A FIG. 3B FIG. 4A FIG. 4B

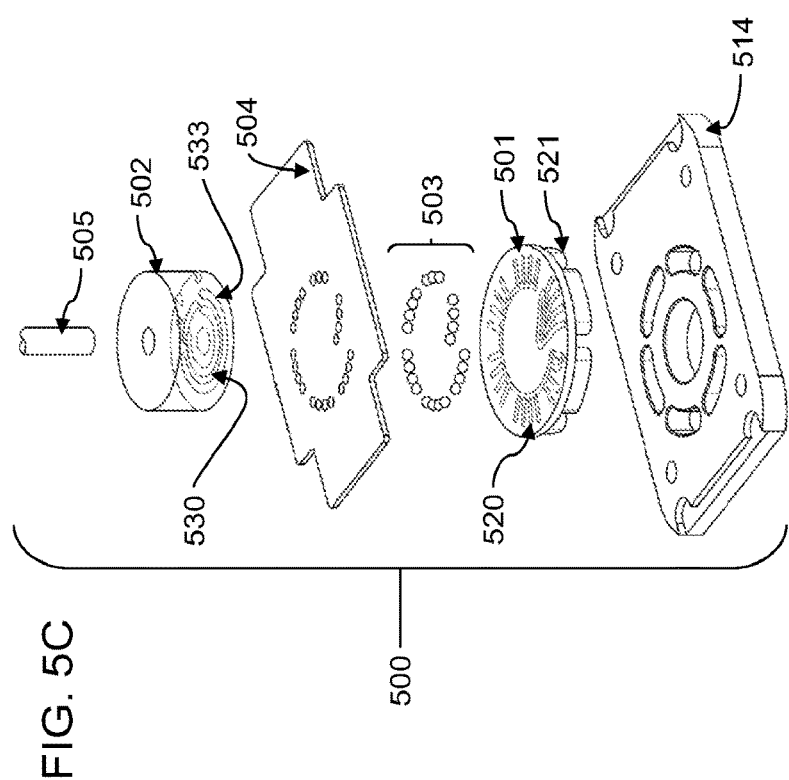
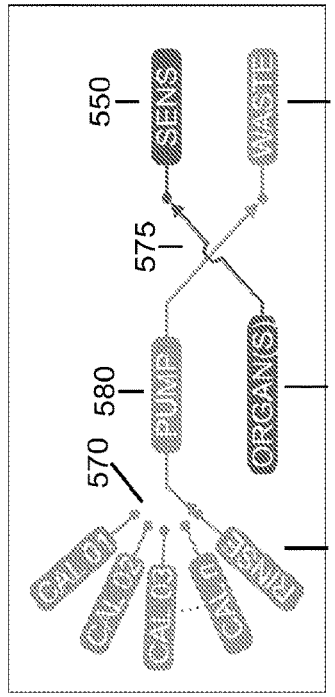
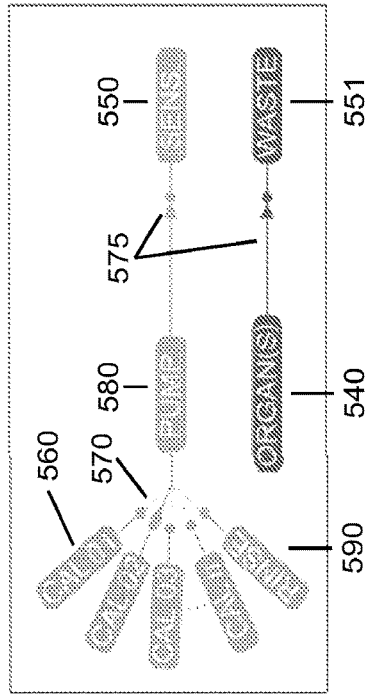
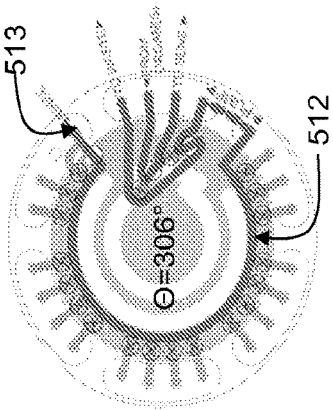
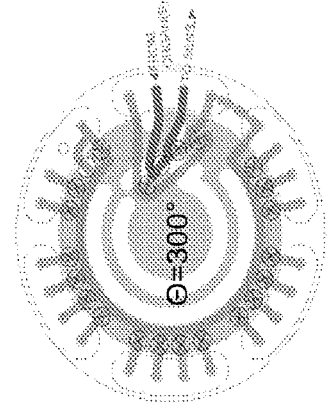
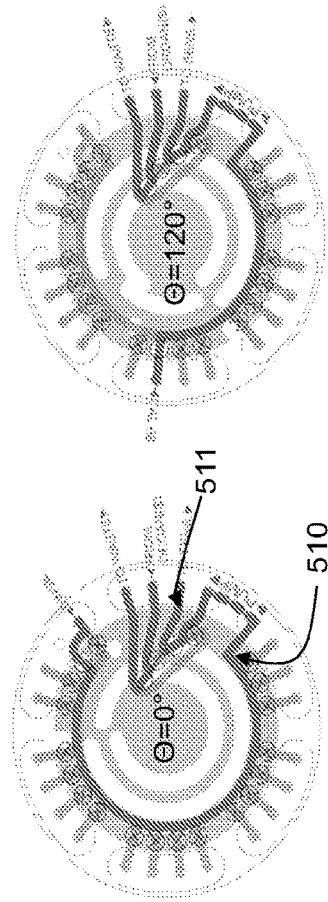
FIG. 5A  FIG. 5B  FIG. 5C  FIG. 5D  FIG. 5E  FIG. 5F  FIG. 5G

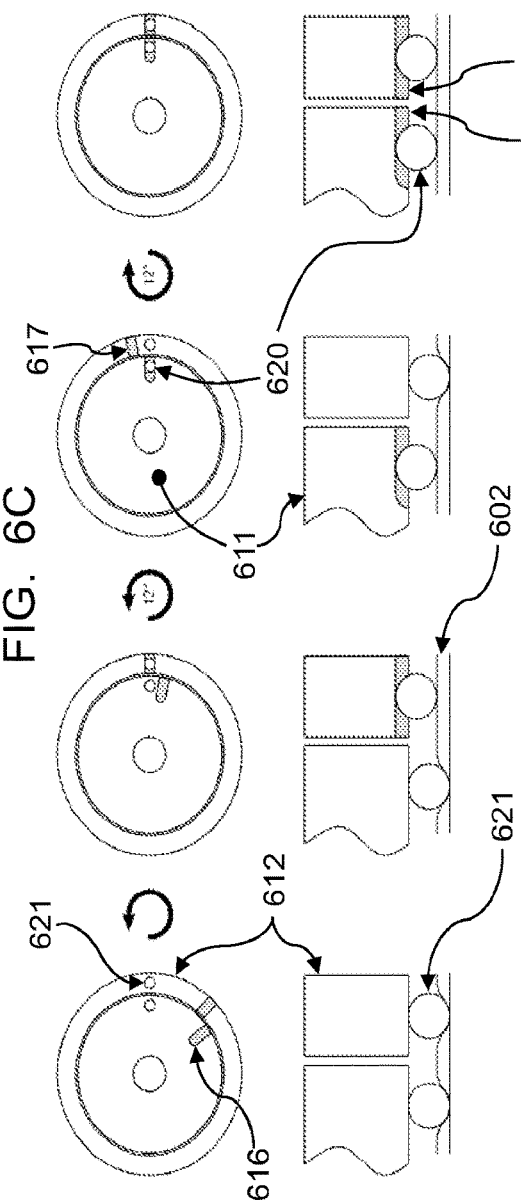
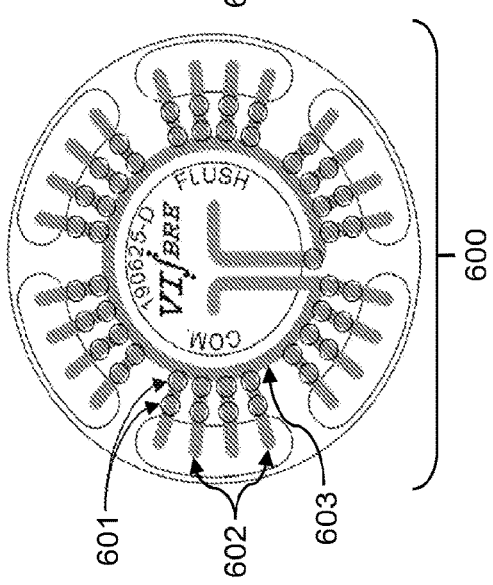
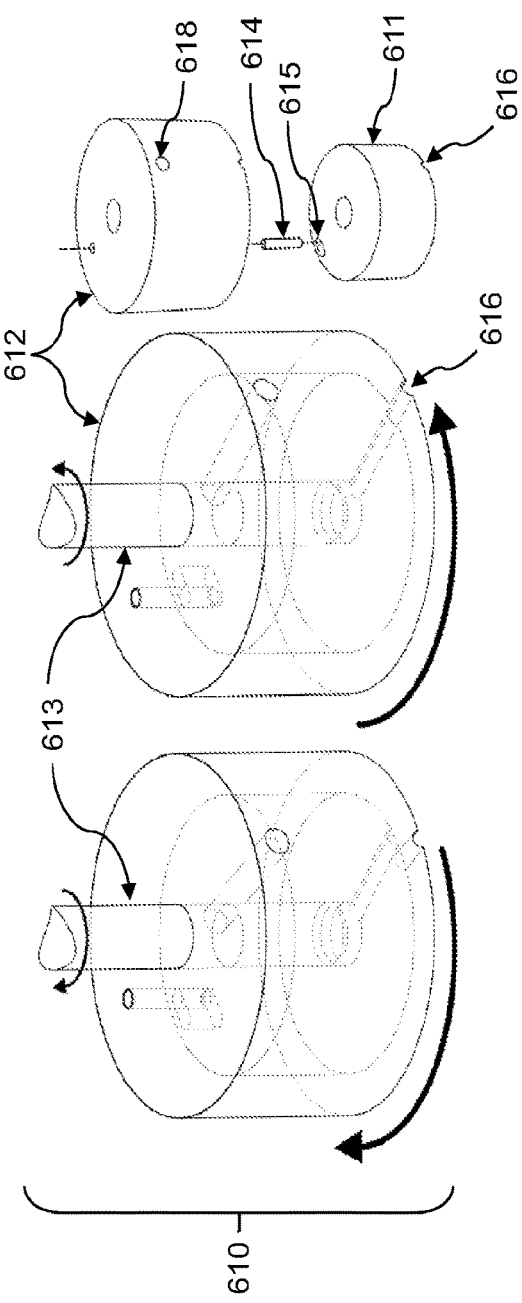

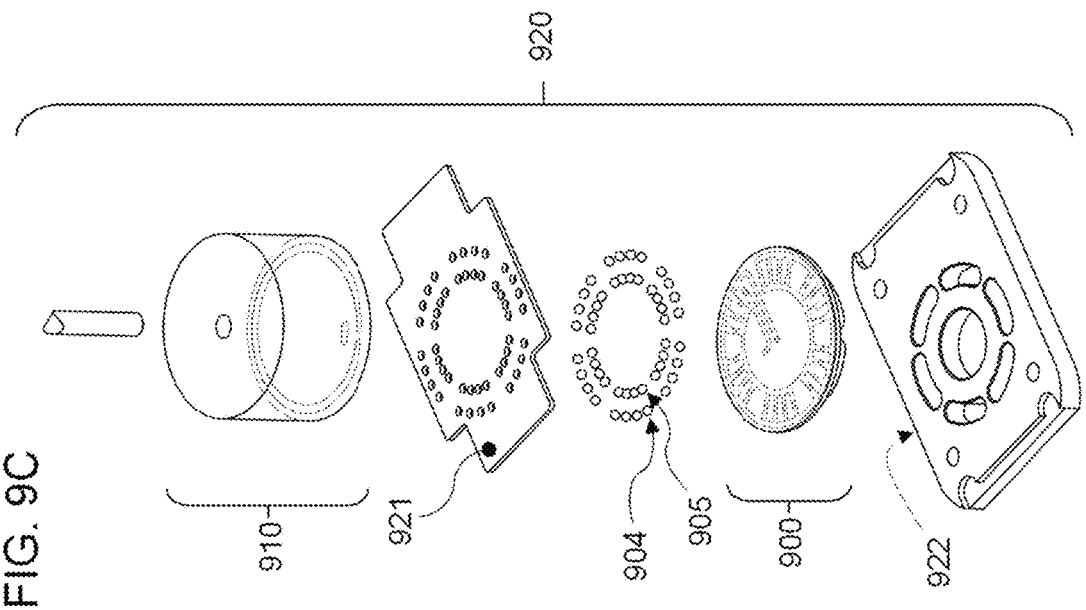
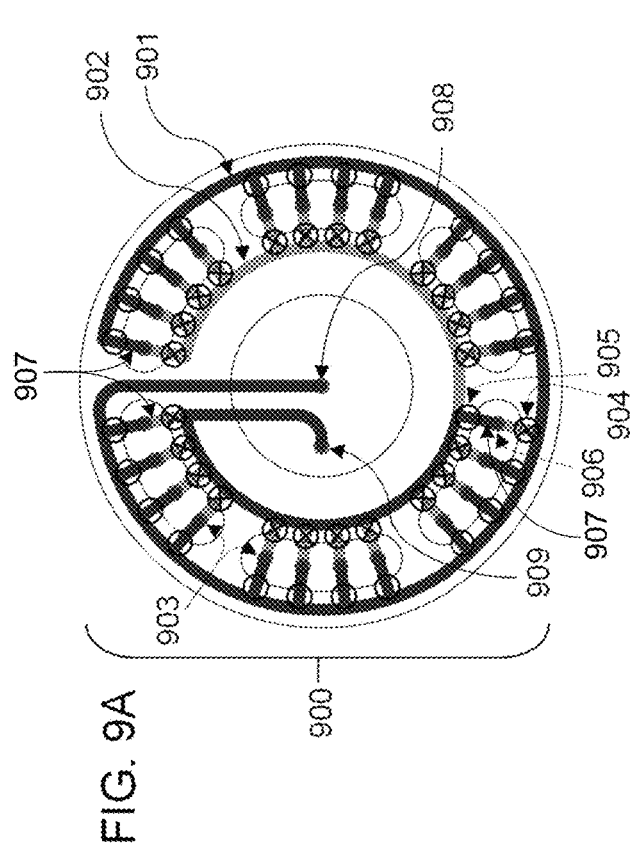
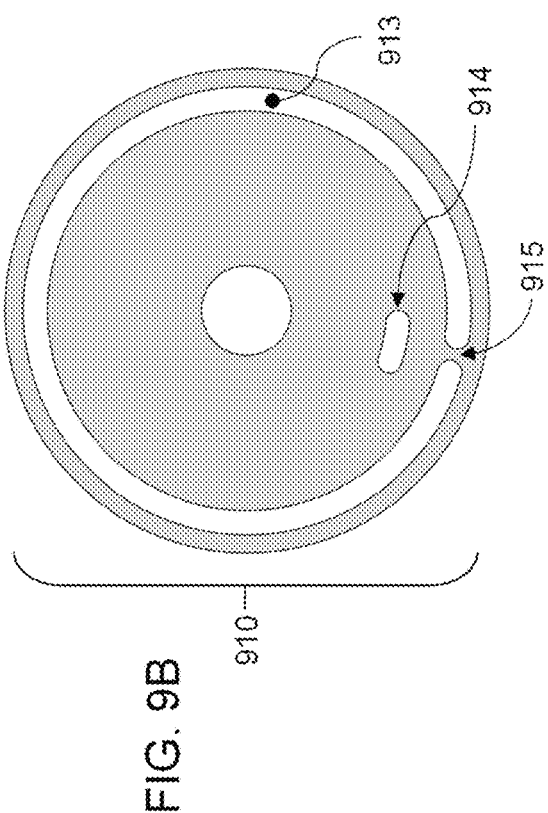

Run Mode

Analysis Mode

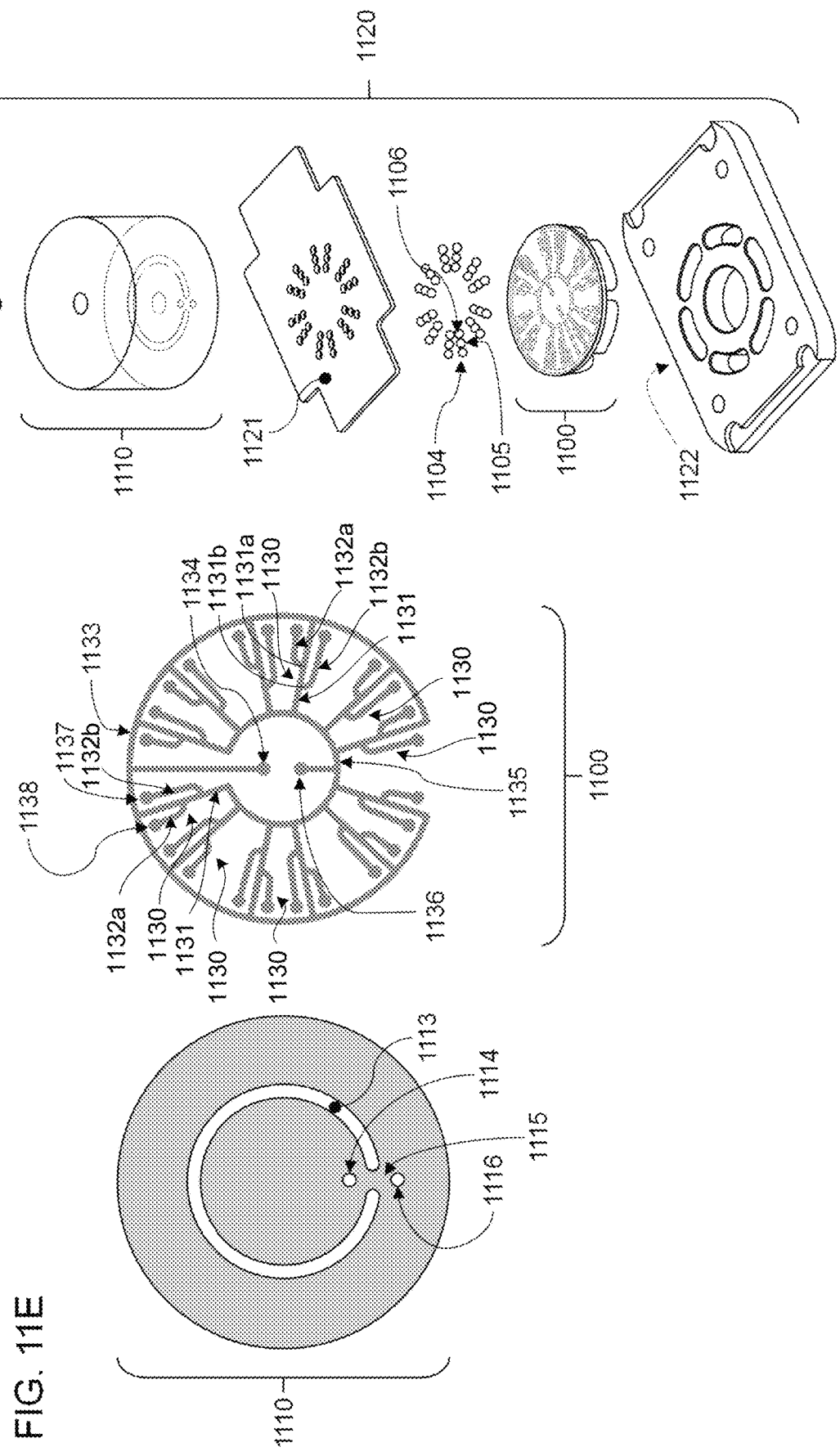

Ball Locations

Internal Actuation Mechanism

Clockwise rotation position

Counterclockwise rotation position

MICROFLUIDIC SYSTEMS FOR MULTIPLE BIOREACTORS AND APPLICATIONS OF SAME

CROSS-REFERENCE TO RELATED PATENT APPLICATIONS

This application claims priority to and the benefit of U.S. Provisional Patent Application Ser. No. 63/053,388, filed Jul. 17, 2020.

This application is also a continuation-in-part application of PCT Patent Application Serial No. PCT/US2020/040061, filed Jun. 29, 2020, which itself claims priority to and the benefit of U.S. Provisional Patent Application Ser. No. 62/868,303, filed Jun. 28, 2019.

This application is also a continuation-in-part application of U.S. patent application Ser. No. 17/269,349, filed Feb. 18, 2021, which is a national stage entry of PCT Patent Application Serial No. PCT/US2019/047307, filed Aug. 20, 2019, which itself claims priority to and the benefit of U.S. Provisional Patent Application Serial Nos. 62/719,868, filed Aug. 20, 2018, and 62/868,303, filed on Jun. 28, 2019.

This application is also a continuation-in-part application of U.S. patent application Ser. No. 17/269,329, filed Feb. 18, 2021, which is a national stage entry of PCT Patent Application Serial No. PCT/US2019/047190, filed Aug. 20, 2019, which itself claims priority to and the benefit of U.S. Provisional Patent Application Serial Nos. 62/719,868, filed Aug. 20, 2018, and 62/868,303, filed on Jun. 28, 2019.

This application is also related to a co-pending PCT patent application, entitled "Microfluidic Systems For Multiple Bioreactors and Applications of Same", which is filed on the same day that this application is filed, and with the same applicant as that of this application.

Each of the above-identified applications is incorporated herein by reference in its entirety.

STATEMENT AS TO RIGHTS UNDER FEDERALLY-SPONSORED RESEARCH

This invention was made with government support under Contract No. HHSN2712017000044C, and Grant Nos. TR002383, TR002243, TR002097, and CA202229, awarded by the National Institutes of Health, Grant No. CBET1706155, awarded by the National Science Foundation, and Grant No. 80NSSC20K0108, awarded by the National Aeronautics and Space Administration. The government has certain rights in the invention.

FIELD OF THE INVENTION

The invention relates generally to fluidic systems, and more particularly to microfluidic systems including valves for multiple bioreactors, and applications of the same.

BACKGROUND OF THE INVENTION

Conventionally, many organs-on-chips are designed to study the physiology of a single organ, and use either height differences in reservoir fluid levels, syringe pumps, on-chip or off-chip peristaltic pumps, or pressurized reservoirs to cause culture media to flow through single- or dual-chamber bioreactors. Many chips have been single-pass, perfused by the pressure from liquid in a pipette tip or a syringe body connected to the chip directly or by a tube. Experiments by others involving recirculation of single-organ or coupled-organ chips typically use rocking gravity perfusion or on-chip pumps. With the recognition that continuous perfusion can be advantageous to batch feeding of individual wells in a cell culture well plate by an array of pipettes, or the individual perfusion of organ chips, organoids, or other microphysiological systems, or multiple parallel microchemostats, it becomes evident that the individual reservoir/bioreactor/pump approach does not scale with regard to space, cost, or complexity.

Therefore, a heretofore unaddressed need exists in the art to address the aforementioned deficiencies and inadequacies.

SUMMARY OF THE INVENTION

One aspect of the present invention relates to a fluidic device. The fluidic device includes a fluidic chip having a fluidic network comprising a plurality of fluidic channels in fluidic communication with a plurality of input ports, at least one output port, and at least one sensing port; and an actuator configured to engage with the fluidic network to control each fluidic channel to switch between an open state in which fluidic flow through said fluidic channel is permitted and a closed state in which no fluidic flow through said fluidic channel is permitted, so as to selectively collect fluid from multiple inputs via the plurality of input ports, and direct either all of the multiple inputs to the at least one output port, or all but a single selected input to the at least one output port and the single selected input to the at least one sensing port to which an analytical instrument is operably connected.

In one embodiment, the plurality of input ports is operably coupled with a plurality of fluidic modules, wherein in operation, the plurality of fluidic modules is individually perfused, and all outputs of the plurality of fluidic modules are directed to the at least one output port, or an output of any one of the plurality of fluidic modules is directed to the at least one sensing port, while outputs of all other fluidic modules are directed to the at least one output port.

In one embodiment, when said output of any one of the plurality of fluidic modules is directed to the analytical instrument, the outputs from all other fluidic modules flow without interruption.

In one embodiment, the plurality of fluidic modules comprises bioreactors, wells, organs-on-chips, chemostats, or a combination of them.

In one embodiment, the fluidic chip has a body in which the fluidic network is formed, and a fluidic chip registration means formed on the body for aligning the fluidic chip with a support structure.

In one embodiment, the fluidic chip registration means is configured such that multiple fluidic chip orientations are allowed while maintaining automatic and precise mechanical alignment to the support structure.

In one embodiment, the fluidic chip is configured such that one or more plug-in accessories are addable in or removable from the fluidic chip.

In one embodiment, the fluidic chip is formed of an elastic material such that compression of the actuator on the body causes at least one of the channels to be occluded.

In one embodiment, the plurality of fluidic channels comprises a first fluidic bus, a second fluidic bus, and a plurality of intermediate channels, each intermediate channel being in fluidic communication with at least one of the plurality of input ports and connected to the first fluidic bus and/or the second fluidic bus.

In one embodiment, the actuator comprises a plurality of actuating elements disposed on the body of the fluidic chip with each actuating element at a location that is over an intermediate channel and is located between a respective port and one of the first fluidic bus and the second fluidic bus to which said intermediate channel is connected, such that compression of said actuating element on the body causes fluidic flow between said respective port and said one of the first fluidic bus and the second fluidic bus through said intermediate channel to be occluded.

In one embodiment, the locations of the plurality of actuating elements on the body of the fluidic chip comprise first locations and second locations, wherein the first locations comprise each actuating element location over a respective intermediate channel between a respective port and the first fluidic bus, and the second locations comprise each actuating element location over a respective intermediate channel between a respective port and the second fluidic bus.

In one embodiment, the actuator further comprises an actuator head for selectively compressing or relaxing each of the plurality of actuating elements.

In one embodiment, the actuator head comprises an outer actuator head having an outer groove corresponding to one of the first locations of the plurality of actuating elements on the body, wherein the outer groove, when aligned with the corresponding one of the first locations, relieves the corresponding actuating element so that the corresponding port is connected to the first fluidic bus; and an inner actuator head sleeved in the outer actuator head, having an inner groove corresponding to one of the second locations of the plurality of actuating elements on the body, wherein the inner groove, when aligned with the corresponding one of the second locations, relieves the corresponding actuating element so that the corresponding port is connected to the second fluidic bus, wherein one of the outer actuator head and the inner actuator head is a driving actuator head driven by a motor, and the other of the outer actuator head and the inner actuator head is a driven actuator head driven by said driving actuator head.

In one embodiment, each of the outer actuator head and the inner actuator head has a circular-segment pocket with a near-360° sweep, wherein the actuator head further comprises a single limiting element, whose motion is constrained by the pockets, allowing the driving actuator head and the driven actuator head to rotate or remain stationary independently until the limiting element contacts opposing ends of both pockets, at which point both actuator heads rotate as one, wherein when the direction of the motor is then reversed, the motion of each of the actuator heads becomes independent again.

In one embodiment, the actuator head comprises a first relief pocket having two ends and a gap defined therebetween, and a second relief aligned with the gap along an intermediate channel, wherein the first relief pocket and the gap are corresponding to the first locations of the plurality of actuating elements on the body of the fluidic chip, and the second relief is corresponding to one of the second locations of the plurality of actuating elements on the body of the fluidic chip, such that in operation, one of the actuating elements on the first locations is pressed by the gap and the others of the actuating elements on the first locations are relaxed by the first pocket, and one of the actuating elements on the second locations is relaxed by the second relief and the others of the actuating elements on the second locations are pressed by the surface of the actuator head, thereby directing the single selected input from the input port connected to said intermediate channel with which the gap and the second relief are aligned to the at least one sensing port through the second fluidic bus, while directing the inputs from all of the other input ports to the at least one output port through the first fluidic bus.

In one embodiment, a rotation of the actuator head at a predetermined angle selects which port is connected to the at least one sensing port, and ensures that all of the other ports are connected to the at least one output port.

In one embodiment, the first fluidic bus comprises two separate sections, each of which is connected to a respective common output port, thereby allowing some of the fluidic channels to have a different common output port so that the inputs from the input ports do not have to mix from every channel.

In one embodiment, the fluidic network further comprises one or more additional ports for flushing the first fluidic bus and/or the second fluidic bus.

In one embodiment, the fluidic device is a direct-access valve or a random-access valve.

In another aspect, the invention relates to a fluidic device comprising: a fluidic chip having a fluidic network comprising a plurality of channel modules, each channel module being in fluidic communication with a pair of input ports, at least one make-up media port, and at least one sensing port; and an actuator configured to engage with the fluidic network to control each channel module to switch between a run mode in which the pair of input ports is fluidically connected to each other, and an analysis mode in which one of the pair of input ports is fluidically connected to the at least one make-up media port, while the other of the pair of input ports is fluidically connected to the at least one sensing port to which an analytical instrument is operably connected.

In one embodiment, the pair of ports of each channel module is operably coupled with a fluidic module and a recirculating pump, such that when said channel module is in the run mode, the fluidic module is fluidically connected to the recirculating pump in a circulating loop, and when said channel module is in the analysis mode, make-up media from the at least one make-up media port is pumped into the fluidic module, and output media from the fluidic module is delivered to the at least one sensing port.

In one embodiment, the fluidic device is configured such that each fluidic module is individually perfusable with its output media directed to the at least one sensing port without disturbing the flow of the others.

In one embodiment, the fluidic module comprises a bioreactor, wells, an organ-on-chip, chemostats, or a combination of them.

In one embodiment, the fluidic chip has a body in which the fluidic network is formed, and a fluidic chip registration means formed on the body for aligning the fluidic chip with a support structure.

In one embodiment, the fluidic chip registration means is configured such that multiple fluidic chip orientations are allowed while maintaining automatic and precise mechanical alignment to the support structure.

In one embodiment, the fluidic chip is configured such that one or more plug-in accessories are addable in or removable from the fluidic chip.

In one embodiment, the fluidic chip is formed of an elastic material such that compression of the actuator on the body causes at least one of the channels to be occluded.

In one embodiment, the fluidic network further comprises a first fluidic bus and a second fluidic bus, and wherein each channel module is connected between the first fluidic bus and the second fluidic bus.

In one embodiment, each channel module has an intermediate channel connected between the first fluidic bus and the second fluidic bus; a first channel connected to the intermediate channel at a first position and one of the pair of input ports; and a second channel connected to the intermediate channel at a second position and the other of the pair of input ports, wherein the first position is between the first fluidic bus and the second position, and the second position is between the first position and the second fluidic bus.

In one embodiment, the actuator comprises a plurality of actuating elements disposed on the body of the fluidic chip, such that compression of an actuating element on the body causes fluidic flow through a corresponding channel portion at which said actuating element is located to be occluded, wherein each of three actuating elements of the plurality of actuating elements are over the intermediate channel of a respective channel module at first, second, and third locations in first, second, and third channel portions of the intermediate channel, respectively, wherein the first channel portion is between the first fluidic bus and the first position, the second channel portion is between the second position and the second fluidic bus, and the third channel portion is between the first and second positions.

In one embodiment, the actuator further comprises an actuator head for selectively compressing or relaxing each of the plurality of actuating elements.

In one embodiment, the actuator head comprises an outer relief for controlling access to the at least one sensing port, an inner relief for controlling access to the at least one make-up media port, and a middle relief pocket having two ends and a gap defined therebetween.

In one embodiment, when the outer relief, the inner relief, and the gap are misaligned with any channel module, all of the first and second actuating elements are pressed by the surface of the actuator head, while all of the third actuating elements are relaxed by the middle relief pocket, so that each channel module is in the run mode. When the outer relief, the inner relief, and the gap are aligned with the intermediate channel of a channel module, the first and second actuating elements on said channel module are relaxed by the first and second reliefs, respectively, and the third actuating element on said channel module is pressed by the gap, all of the first and second actuating elements on the other channel modules are pressed by the surface of the actuator head, while all of the third actuating elements on the other channel modules are relaxed by the middle relief pocket, so that said channel module is in the analysis mode and all of the other channel modules are in the run mode.

In one embodiment, a rotation of the actuator head at a predetermined angle selects which channel module is in the analysis mode.

In one embodiment, replacement fluid can be injected into the output line of the isolated module without disturbing the flows of the other fluidic modules.

In one embodiment, the fluidic network further comprises one or more additional ports for flushing the first fluidic bus and/or the second fluidic bus.

In one embodiment, the fluidic device is a direct-access valve or a random-access valve.

These and other aspects of the invention will become apparent from the following description of the preferred embodiment taken in conjunction with the following drawings, although variations and modifications therein may be affected without departing from the spirit and scope of the novel concepts of the disclosure.

BRIEF DESCRIPTION OF THE DRAWINGS

The accompanying drawings illustrate one or more embodiments of the invention and, together with the written description, serve to explain the principles of the invention. Wherever possible, the same reference numbers are used throughout the drawings to refer to the same or like elements of an embodiment.

FIGS. 1A-1F show schematically examples of single bioreactor perfusion topologies.

FIGS. 3A-3B show schematically a circular, through-plate valve, according to embodiments of the invention.

FIGS. 4A-4B show schematically another circular, through-plate valve, according to embodiments of the invention.

FIGS. 5A-5G show schematically an analytical valve, according to embodiments of the invention.

FIGS. 6A-6C show schematically a lagging actuator random-access valve, according to embodiments of the invention.

FIGS. 9A-9J show schematically a sensing valve.

FIGS. 11A-11M show schematically a cut-in valve, according to embodiments of the invention.

DETAILED DESCRIPTION OF THE INVENTION

Figure 2A:
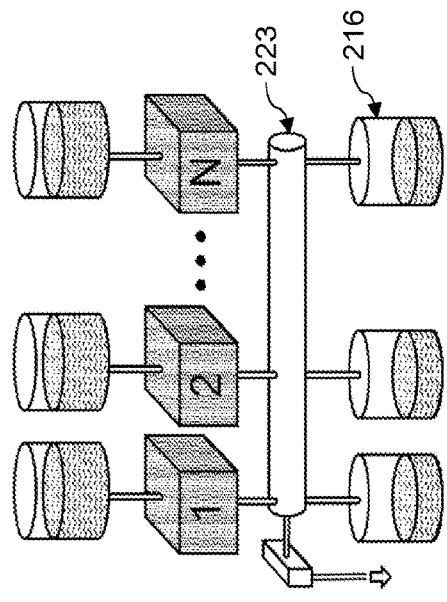
FIGS. 2A-2D show schematically examples of multiple bioreactor sensing valves.

The invention will now be described more fully hereinafter with reference to the accompanying drawings, in which exemplary embodiments of the invention are shown. The invention may, however, be embodied in many different forms and should not be construed as limited to the embodiments set forth herein. Rather, these embodiments are provided so that this disclosure will be thorough and complete, and will fully convey the scope of the invention to those skilled in the art. Like reference numerals refer to like elements throughout.

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting and/or capital letters has no influence on the scope and meaning of a term; the scope and meaning of a term are the same, in the same context, whether or not it is highlighted and/or in capital letters. It will be appreciated that the same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification, including examples of any terms discussed herein, is illustrative only and in no way limits the scope and meaning of the invention or of any exemplified term. Likewise, the invention is not limited to various embodiments given in this specification.

It will be understood that when an element is referred to as being "on" another element, it can be directly on the other element or intervening elements may be present therebetween. In contrast, when an element is referred to as being "directly on" another element, there are no intervening elements present. As used herein, the term "and/or" includes any and all combinations of one or more of the associated listed items.

It will be understood that, although the terms first, second, third, etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below can be termed a second element, component, region, layer or section without departing from the teachings of the invention.

It will be understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "adjacent" to another feature may have portions that overlap or underlie the adjacent feature.

The terminology used herein is for the purpose of describing particular embodiments only and is not intended to be limiting of the invention. As used herein, the singular forms "a," "an," and "the" are intended to include the plural forms as well, unless the context clearly indicates otherwise. It will be further understood that the terms "comprises" and/or "comprising," or "includes" and/or "including" or "has" and/or "having" when used in this specification specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom" and "upper" or "top," may be used herein to describe one element's relationship to another element as illustrated in the figures. It will be understood that relative terms are intended to encompass different orientations of the device in addition to the orientation shown in the figures. For example, if the device in one of the figures is turned over, elements described as being on the "lower" side of other elements would then be oriented on the "upper" sides of the other elements. The exemplary term "lower" can, therefore, encompass both an orientation of lower and upper, depending on the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

Unless otherwise defined, all terms (including technical and scientific terms) used herein have the same meaning as commonly understood by one of ordinary skill in the art to which the invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

As used herein, "around," "about," "substantially" or "approximately" shall generally mean within 20 percent, preferably within 10 percent, and more preferably within 5 percent of a given value or range. Numerical quantities given herein are approximate, meaning that the terms "around," "about," "substantially" or "approximately" can be inferred if not expressly stated.

As used herein, the terms "comprise" or "comprising," "include" or "including," "carry" or "carrying," "has/have" or "having," "contain" or "containing," "involve" or "involving" and the like are to be understood to be open-ended, i.e., to mean including but not limited to.

As used herein, the phrase "at least one of A, B, and C" should be construed to mean a logical (A or B or C), using a non-exclusive logical OR. As used herein, the term "and/or" includes any and all combinations of one or more of the associated listed items.

The description below is merely illustrative in nature and is in no way intended to limit the invention, its application, or uses. The broad teachings of the invention can be implemented in a variety of forms. Therefore, while this invention includes particular examples, the true scope of the invention should not be so limited since other modifications will become apparent upon a study of the drawings, the specification, and the following claims. For purposes of clarity, the same reference numbers will be used in the drawings to identify similar elements. It should be understood that one or more steps within a method may be executed in different order (or concurrently) without altering the principles of the invention.

Historically, many organs-on-chips are designed to study the physiology of a single organ, and use either height differences in reservoir fluid levels, syringe pumps, on-chip or off-chip peristaltic pumps, or pressurized reservoirs to cause culture media to flow through single- or dual-chamber bioreactors. Many chips have been single-pass, perfused by the pressure from liquid in a pipette tip or a syringe body connected to the chip directly or by a tube. Experiments by others involving recirculation of single-organ or coupled-organ chips typically use rocking gravity perfusion or on-chip pumps. FIGS. 1A-1F show five different configurations of reservoir/bioreactor assemblies that are in common use.

FIG. 1A shows gravity-reservoir, single-chamber bioreactor assembly 100, which comprises a supply reservoir 106 containing supply media 107 and connected by tubing 108 to single-chamber bioreactor 109. The effluent media is delivered by tubing to selector valve 120 that delivers sample to on-line media analyzer 121 whose analyzed media 127 is sent to waste. The media not sent to the analyzer 121 is passed on to collection reservoir 116 containing collected media 117 that can be analyzed off-line or sent to waste.

FIG. 1B shows a gravity-reservoir, dual-chamber bioreactor assembly 101 that uses two input reservoirs 106 to perfuse dual-chamber bioreactor 118 whose media is sent either to a pair of analyzers 121 or to separate waste containers 116.

FIG. 1C shows a pumped, dual-reservoir single-chamber bioreactor assembly 102 that utilizes pump 130 to return collected media 117 to the supply reservoir 106 via return tubing 138.

FIG. 1D shows a pumped, single-reservoir single-chamber bioreactor assembly 103 for which the pump 130 directly delivers media to the bioreactor 109.

FIG. 1E shows an assembly 104 comprising a plurality of N gravity-reservoir, single-chamber bioreactors, each of which has its own supply and collection reservoirs, selector valve, and analyzer.

FIG. 1F shows a similar assembly 105 comprising a plurality of N pumped, single-reservoir, single-chamber bioreactors with only one reservoir for each bioreactor.

With the recognition that continuous perfusion can be advantageous to batch feeding of individual wells in a cell culture well plate by an array of pipettes, or the individual perfusion of organ chips, organoids, or other microphysiological systems, or multiple parallel bioreactors, including chemostats and microchemostats, it becomes evident that the individual reservoir/bioreactor/pump approach shown in FIGS. 1A-1F does not scale with regard to space, cost, or complexity. The shortcoming of this approach can be addressed with the use of multichannel pumps and valves that are designed specifically to meet the needs of the controlled perfusion of well plates, microphysiological bioreactors, or chemostats, as shown schematically in FIGS. 2A-2D.

FIG. 2A shows an assembly 204 comprising a plurality of N gravity-reservoir, single-chamber bioreactors, where each bioreactor 209 has a supply reservoir 206 containing supply media 207 and connected by tubing 208 to the common multichannel selector valve 222 with a common collection reservoir 216 containing collected media 217 that can be analyzed off-line or sent to waste. The multichannel selector valve 222 is also connected by sample analysis port/line 220 to on-line media analyzer 221 whose analyzed media 227 is sent to waste.

Figure 2B:
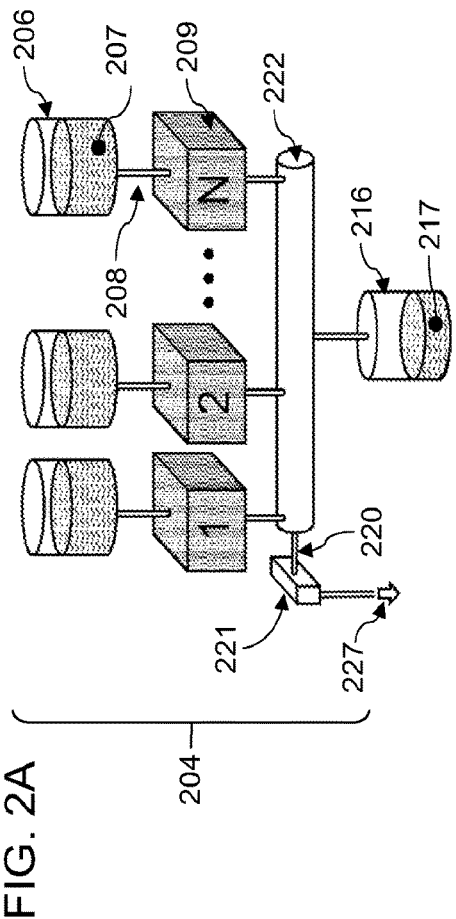

FIG. 2B shows a similar assembly 204 that differs from that in FIG. 2A by the use of a multichannel selector valve 223 with N separate collection reservoirs 216 and a single sample analysis port and line 220.

Figure 2C:
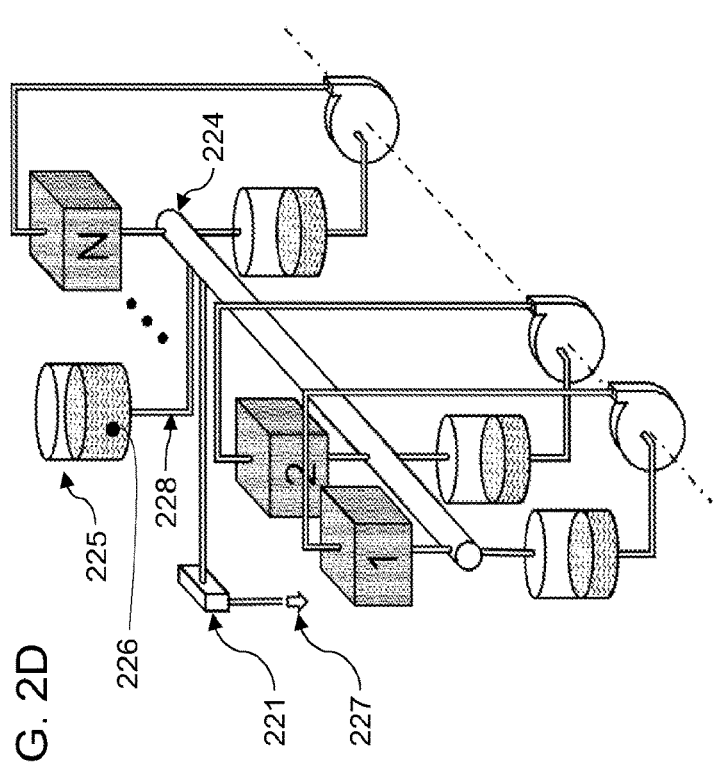

FIG. 2C shows an assembly 205 comprising a plurality of N pumped, single-reservoir, single-chamber bioreactors 209 with N tubes 208 connected to the N-channel selector valve 223 with separate collection reservoirs 216. A multi-channel pump 231 is comprised of N pumps 230 operating in parallel to return collected media 217 from each collection reservoir 216 directly to the corresponding bioreactor 209 via return tubing 238. Hence there are N bioreactors, N sets of tubing 208 and 238 (which could be configured as ribbon tubing), and an N-channel pump, with all of the N media streams being analyzed by on-line media analyzer 221.

Figure 2D:
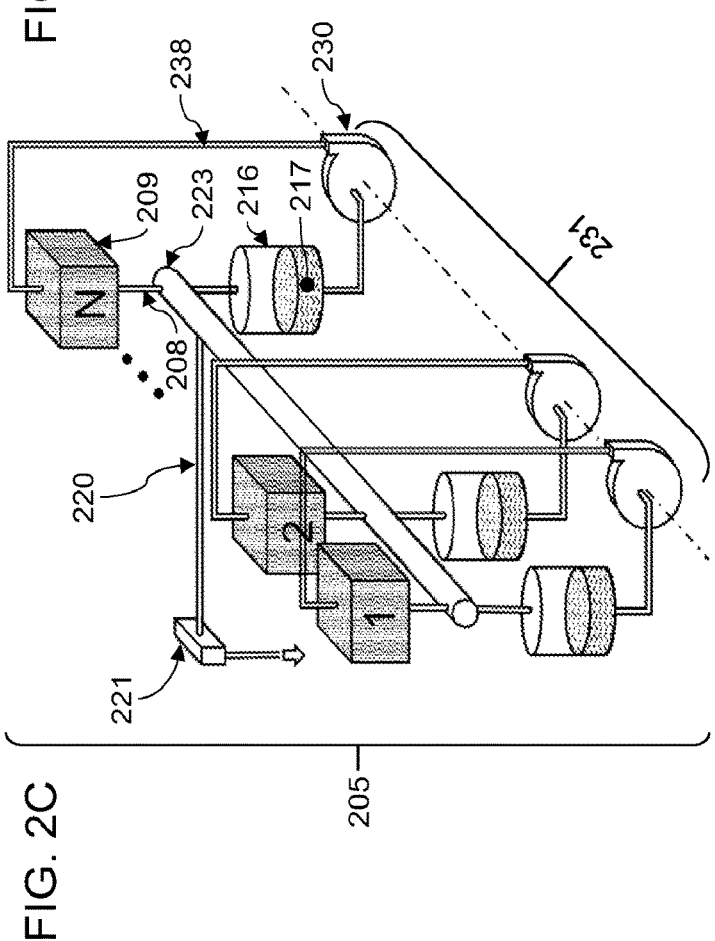

FIG. 2D shows a configuration similar to that of FIG. 2C, except that the N-channel selector valve 224 connects not only to the separate collection reservoirs, but also via media make-up line 228 to a make-up media reservoir 225 filled with make-up media 226 to replace the analyzed media 227 that is sent to waste when a particular reservoir is being sampled for analysis by analyzer 221.

We have previously described multi-port valves that serve a variety of functions in perfusing organs-on-chips and delivering and removing fluid from individual wells in a well plate, as might be needed for a microclinical analyzer or microformulator. As we will see, the requirements for the parallel access valves shown in FIGS. 2A-2D cannot be met with our previous valve designs, for example, the 25-port valve shown in FIGS. 3A-3B and 4A-4B, the analytical valve shown in FIGS. 5A-5G, and the random-access valve shown in FIGS. 6A-6C, which are disclosed originally in U.S. patent application Ser. No. 17/269,329, and PCT Patent Application Serial No. PCT/US2020/040061, which are incorporated herein by reference in their entireties.

FIGS. 3A-3B are perspective and plan views of a circular through-plate 25-channel valve fluidic chip 301, showing an actuated surface, working channels 333, registration/alignment protrusions 306, and interface ports 302, according to one embodiment of the invention.

FIG. 4A shows an enclosed valve cartridge 400 according to one embodiment of the invention. This configuration utilizes the position data provided by motor encoder 439 to align a valve actuator 416 in order to open specific channels in the valve fluidic chip 401. The valve actuator 416 is a cylinder made from acetal resin or other material. Topography on the lower face of the valve actuator 416, such as a groove 417, pockets, or similar features, displaces balls 418 as the actuator 416 is rotated. The ball cage 419 constrains movements of the balls 418 to the vertical axis via holes 420 within which the balls reside. The ball cage 419 is constrained against interior faces of surrounding standoff plates/tabs/flanges 406, thereby preventing rotational movement of the ball cage 419 and the balls 418. The surrounding standoff plates/tabs/flanges 406 allows for multiple chip orientations while maintaining automatic and precise mechanical alignment. The balls 418 that are forced into the surface of the fluidic chip 401 compress the channel (not pictured here) in each ball's immediate proximity, thereby pinching off and closing those channels to fluid movement. The fluidic chip 401 is held in position by the openings 456 in the fluidics plate 440. FIG. 4B shows an expanded, exploded view of a 25-channel valve subassembly according to one embodiment of the invention.

Given the need to remove media from a single bioreactor and deliver it to a sensor for analysis, and also sequentially deliver one or more calibration solutions to the sensor, a multi-port, multi-throw analytical valve, as shown in FIGS. 5A-5G, is disclosed according to certain embodiments of the invention. Specifically, FIGS. 5A and 5B show the operation and utility of the multi-port, multi-throw analytical valve to control the connection of the output flow of one or more perfused microbioreactors, chemostats, or organ chips 540 to a metabolic or other sensor 550 or a waste reservoir 551. During the operation of the analytical valve in either a measurement mode (FIG. 5A) or a calibration mode (FIG. 5B), the output flow of the bioreactor(s) is never blocked. As shown in FIG. 5A, in the measurement mode, the output of the organ(s) 540 passes through the sensor 550 by the position of the valve 575, and the common fluidic channels of the valve 575 and the pump 580 are rinsed by having the pump 580 withdraw rinse media from reservoir 590 and direct it towards the waste reservoir 551. Other calibration solutions 560 could be pumped to the waste reservoir 551 as well, depending upon the position of valve 570. Further, as shown in FIG. 5B, in order to calibrate the metabolic sensor 550, which is prone to drift, the valve 575 is switched to the calibration mode and valve 570 is used to select calibration media (CAL 02 shown) from one of several calibration media reservoirs 560 to perform the calibration operation, the calibration media is delivered to the sensor 550 by the pump 580, and the output(s) of the organ(s) 540 is directed towards the waste 551 by the action of the valve 575. In this design, the organ(s) may be perfused by gravity, pneumatic pressure, or a pump (not shown) such that the organ is always continuously perfused.

FIG. 5C shows a single microfluidic analytical valve 500 that can implement the various modes described in FIGS. 5A and 5B with a single actuator and motor. As shown in FIG. 5C, the analytical valve 500 includes a fluidic chip 501 with protrusions 521 that serve as tubing ports and anchor the fluidic chip 501 to the support plate 514, and microfluidic channels in the fluidic network 520 are sealed within the fluidic chip 501. The actuator 502, with ball-actuating grooves 530 in an actuating surface 533, is driven by a motor shaft 505, and includes actuating elements 503, a ball cage 504, and an off-board pump (not shown). The actuator 502 rotates to change the state of the valve as the caged actuating elements (in this embodiment balls) slide against the actuator. For example, in a first state as shown in FIG. 5D (where an actuator angle Θ=0°), the analytical valve 500 collects an analyte from the bioreactor (not shown) through a bioreactor input channel, and sends it to a waste reservoir (not shown) through a waste output channel, while also collecting a rinse solution and directing it first through an internal fluidic channel 510, the off-board pump (not shown), through another internal fluidic channel 511, and finally to the sensor (not shown) through a sensor output channel. In a second state as shown in FIG. 5E (where the actuator angle Θ=120°), a calibration solution is selected (e.g., CAL 08) through a corresponding calibration input channel and directed to the sensor through the sensor output channel, while the bioreactor input channel is interconnected to the waste output channel to send the effluent from the bioreactor to waste. In a third state (where the actuator angle Θ=252-285°, not shown), the effluent is directed from the bioreactor to waste, while all other conduits are closed and idle. In a fourth state as shown in FIG. 5F (where the actuator angle)Θ=300°, the bioreactor input channel is switched and interconnected to the sensor output channel to direct the effluent from the bioreactor to the sensor for analysis, while all other conduits are idle. In a fifth state as shown in FIG. 5G (where the actuator angle Θ=306°), a rinse solution is directed through a rinse input channel to pass the length of channels 512 and 513 and sent to waste, while the effluent is collected from the bioreactor and sent to the sensor. In the embodiments as shown in FIGS. 5A-5G, the analytical valve 500 is designed such that fluid being pumped into the fluidic chip 501 from the bioreactor as effluent has an outlet at all times (either sent to the sensor, to waste, or to both), as not to cause a dead-end scenario that might rupture the fluidic chip 501 or interrupt perfusion of a sensitive organ chip. In certain embodiments, the number of ports or channels that can be serviced as shown in FIGS. 5C-5G is determined by the available circumference of the through-plate fluidic chip 501 and the underlying tubing-port protrusions 521 that anchor the fluidic chip 501 to the support plate 514, and the minimum spacing between individual channels in the fluidic network 520. As shown in FIG. 5C, a typical valve has 1 inlet/outlet port and 25 outlet/inlet ports, depending upon the chosen flow direction. In certain embodiments, different designs of the fluidic network 520 could use some of the 23 channels to service two or more independent bioreactors whose output is either sent to a sensor or waste.

Both of the valves shown in FIGS. 4A-4B and 5A-5G are serial access, i.e., the channels are opened and closed in sequence, so that if the valve has channel 4 open but instead it is necessary to open channel 6, with these valves the actuator must be turned until channel 4 is closed, followed by channel 5 being opened, then channel 5 closed, and finally channel 6 is opened.

FIGS. 6A-6C show how a lagging-actuator random-access (also called direct-access) valve 600 utilizes a two-part actuator with control over rotational direction and range to randomly access any channel in the valve 600, according to certain embodiments of the invention. Specifically, the rotary valves described above are all serial access valves, with the ports being addressed one after another as the actuator is rotated. As long as the fluidic channels were not pressurized and the actuator was rotated quickly, there would be minimal fluid displaced from channels during rotation. As an alternative, the lagging-actuator random-access valve has the ability to go from one valve position to a distant one without having to transiently open and close each intermediate channel. As shown in FIG. 6A, a valve chip 600 has multiple actuating element (ball) locations 601 operating on each of the input/output fluidic channels 602 connected to a common fluidic channel 603. Each input/output fluidic channel 602 is normally pinched closed by two radially adjacent balls 620 and 621 (see FIG. 6C). A given input/output channel 602 pinched by at least one ball 620 or 621 is closed. In order to open the given input/output channel 602, the compressive force applied to both corresponding balls 620 and 621 must be relieved concurrently. In other words, if either or both balls 620 and 621 are not actuated from their normally-closed position, the channel 602 remains closed.

FIG. 6B shows a lagging-actuator assembly 610, including an inner (driven) actuator 611 and an outer (driving) actuator 612, as coaxially aligned on a motor shaft 613. The outer actuator 612 is locked to the motor shaft 613 by a set screw (not shown) in the screw hole 618.

A limiting pin 614 is affixed to the outer actuator 612, and its motion is constrained within the bounds of a limiting pocket 615 on the inner actuator 611. When the outer actuator 612 is rotated clockwise, the limiting pin 614 is driven to the clockwise extreme end of the limiting pocket 615, and the reverse is also true. The arc-length of the limiting pocket 615 establishes an intended backlash or "lag" between the outer actuator 612 and the inner actuator 611. As the outer actuator 612 rotates clockwise as viewed from above, the limiting pin 614 contacts clockwise the extreme end of the limiting pocket 615, and the outer actuator 612 and the inner actuator 611 begin to rotate as a whole, with an outer groove 617 on the outer actuator 612 and an inner groove 616 on the inner actuator 611 unaligned. With the grooves 616 and 617 unaligned, all input/output channels 602 see compression from at least one ball 620 and 621 at all times.

Beginning in this state and immediately following reversal in a rotational direction of the outer actuator 612, the inner actuator 611 remains stationary (by friction and/or presence of the actuator element 620 within the inner groove 616) until the limiting pin 614 contacts the other end of the limiting pocket 615, and the inner actuator 611 and the outer actuator 612 rotate as a whole with the grooves 616 and 617 axially aligned. In this case, with the actuator grooves 616, 617 axially aligned, both pinch points established by the balls 620 and 621 are relieved concurrently, and the target channel 602 opens to flow.

FIG. 6C shows a lagging-actuator assembly 610 as seen by the fluidic chip 600 as well as corresponding cross-sectional views, in multiple steps (from left to right) required for opening target channel 602 to flow. As the grooves 616 and 617 approach a target zone, the inner ball 620 and the outer ball 621 remain pressed into the fluidic chip, thereby blocking flow. When the lagging-actuator assembly 610 rotates from its previous position, no channel has both balls released concurrently. In the second step, by rotating counterclockwise (as seen by the fluidic chip 600), the outer groove 617 reaches and aligns with the outer ball 621. In the third step, after further counterclockwise rotation, the outer groove 617 has rotated past alignment with the outer ball 621, while the inner groove 616 reaches and aligns with the inner ball 620. In the rightmost and last step, rotation reverses until the outer groove 617 also aligns with the outer ball 621 while the inner (driven) actuator 611 remains stationary. Both balls have now retracted to open the target channel 602.

In a different application, the actuator assembly 610 may spin along a same direction continuously (rather than moving to a designated channel and stopping) with the grooves unaligned, causing the balls 620 and 621 to sequentially relax momentarily. As the pinched channels 602 momentarily relax, the fluid previously displaced by respective balls 620 and 621 returns to fill the void. As the actuator assembly 610 continues to rotate, the balls 620 and 621 once again pinch the channel 602, and the corresponding fluid is again displaced. The result is a pulsation of fluid through the conduit within and/or connected to the channel 602, and this pulsation could be used at the end of the conduit to mix or agitate a reservoir of liquid in which it is submerged. Since no channels are relieved of both pinch points concurrently in this application, there is no net flow through channels 602. In yet another application, it is also possible to provide the sequence required for unidirectional pumping by employing concentric rings that have a small "lag" offset. By making the lag offset operate in both directions, the sequence will be the same on the fluidic no matter which direction the motor is turning. This could be useful when coupling other mechanical components that are direction sensitive and could allow different modes of operation while always pumping fluid in the same direction.

One of the objectives of the invention is to develop valves that would allow a portion of the effluent from any and/or all of a plurality of bioreactors or chemostats to be sent to a common analytical instrument while the effluent from all other bioreactors or chemostats flows without interruption.

In one aspect, the invention relates to a fluidic device. The fluidic device includes a fluidic chip having a fluidic network comprising a plurality of fluidic channels in fluidic communication with a plurality of input ports, at least one output port, and at least one sensing port; and an actuator configured to engage with the fluidic network to control each fluidic channel to switch between an open state in which fluidic flow through said fluidic channel is permitted and a closed state in which no fluidic flow through said fluidic channel is permitted, so as to selectively collect fluid from multiple inputs via the plurality of input ports, and direct either all of the multiple inputs to the at least one output port, or all but a single selected input to the at least one output port and the single selected input to the at least one sensing port to which an analytical instrument is operably connected.

In some embodiments, the plurality of input ports is operably coupled with a plurality of fluidic modules, wherein in operation, the plurality of fluidic modules is individually perfused, and all outputs of the plurality of fluidic modules are directed to the at least one output port, or an output of any one of the plurality of fluidic modules is directed to the at least one sensing port, while outputs of all other fluidic modules are directed to the at least one output port.

In some embodiments, when said output of any one of the plurality of fluidic modules is directed to the analytical instrument, the outputs from all other fluidic modules flow without interruption.

In some embodiments, the plurality of fluidic modules comprises bioreactors, chemostats, wells, organs-on-chips, or a combination of them.

In some embodiments, the fluidic chip has a body in which the fluidic network is formed, and a fluidic chip registration means formed on the body for aligning the fluidic chip with a support structure.

In some embodiments, the fluidic chip registration means is configured such that multiple fluidic chip orientations are allowed while maintaining automatic and precise mechanical alignment to the support structure.

In some embodiments, the fluidic chip is configured such that one or more plug-in accessories are addable in or removable from the fluidic chip.

In some embodiments, the fluidic chip is formed of an elastic material such that compression of the actuator on the body causes at least one of the channels to be occluded.

In some embodiments, the plurality of fluidic channels comprises a first fluidic bus, a second fluidic bus, and a plurality of intermediate channels, each intermediate channel being in fluidic communication with at least one of the plurality of input ports and connected to the first fluidic bus and/or the second fluidic bus.

In some embodiments, the actuator comprises a plurality of actuating elements disposed on the body of the fluidic chip with each actuating element at a location that is over an intermediate channel and is located between a respective port and one of the first fluidic bus and the second fluidic bus to which said intermediate channel is connected, such that compression of said actuating element on the body causes fluidic flow between said respective port and said one of the first fluidic bus and the second fluidic bus through said intermediate channel to be occluded.

In some embodiments, the locations of the plurality of actuating elements on the body of the fluidic chip comprise first locations and second locations, wherein the first locations comprise each actuating element location over a respective intermediate channel between a respective port and the first fluidic bus, and the second locations comprise each actuating element location over a respective intermediate channel between a respective port and the second fluidic bus.

In some embodiments, the actuator further comprises an actuator head for selectively compressing or relaxing each of the plurality of actuating elements.

In some embodiments, the actuator head comprises an outer actuator head having an outer groove corresponding to one of the first locations of the plurality of actuating elements on the body, wherein the outer groove, when aligned with the corresponding one of the first locations, relieves the corresponding actuating element so that the corresponding port is connected to the first fluidic bus; and an inner actuator head sleeved in the outer actuator head, having an inner groove corresponding to one of the second locations of the plurality of actuating elements on the body, wherein the inner groove, when aligned with the corresponding one of the second locations, relieves the corresponding actuating element so that the corresponding port is connected to the second fluidic bus, wherein one of the outer actuator head and the inner actuator head is a driving actuator head driven by a motor, and the other of the outer actuator head and the inner actuator head is a driven actuator head driven by said driving actuator head.

In some embodiments, each of the outer actuator head and the inner actuator head has a circular-segment pocket with a near-360° sweep, wherein the actuator head further comprises a single limiting element, whose motion is constrained by the pockets, allowing the driving actuator head and the driven actuator head to rotate or remain stationary independently until the limiting element contacts opposing ends of both pockets, at which point both actuator heads rotate as one, wherein when the direction of the motor is then reversed, the motion of each of the actuator heads becomes independent again.

In some embodiments, the actuator head comprises a first relief pocket having two ends and a gap defined therebetween, and a second relief aligned with the gap along an intermediate channel, wherein the first relief pocket and the gap are corresponding to the first locations of the plurality of actuating elements on the body of the fluidic chip, and the second relief is corresponding to one of the second locations of the plurality of actuating elements on the body of the fluidic chip, such that in operation, one of the actuating elements on the first locations is pressed by the gap and the others of the actuating elements on the first locations are relaxed by the first pocket, and one of the actuating elements on the second locations is relaxed by the second relief and the others of the actuating elements on the second locations are pressed by the surface of the actuator head, thereby directing the single selected input from the input port connected to said intermediate channel with which the gap and the second relief are aligned to the at least one sensing port through the second fluidic bus, while directing the inputs from all of the other input ports to the at least one output port through the first fluidic bus.

In some embodiments, a rotation of the actuator head at a predetermined angle selects which port is connected to the at least one sensing port, and ensures that all of the other ports are connected to the at least one output port.

In some embodiments, the first fluidic bus comprises two separate sections, each of which is connected to a respective common output port, thereby allowing some of the fluidic channels to have a different common output port so that the inputs from the input ports do not have to mix from every channel.

In some embodiments, the fluidic network further comprises one or more additional ports for flushing the first fluidic bus and/or the second fluidic bus.

In some embodiments, the fluidic device is a direct-access valve or a random-access valve.

In another aspect, the invention relates to a fluidic device comprising: a fluidic chip having a fluidic network comprising a plurality of channel modules, each channel module being in fluidic communication with a pair of input ports, at least one make-up media port, and at least one sensing port; and an actuator configured to engage with the fluidic network to control each channel module to switch between a run mode in which the pair of input ports is fluidically connected to each other, and an analysis mode in which one of the pair of input ports is fluidically connected to the at least one make-up media port, while the other of the pair of input ports is fluidically connected to the at least one sensing port to which an analytical instrument is operably connected.

In some embodiments, the pair of ports of each channel module is operably coupled with a fluidic module and a recirculating pump, such that when said channel module is in the run mode, the fluidic module is fluidically connected to the recirculating pump in a circulating loop, and when said channel module is in the run mode, make-up media from the at least one make-up media port is pumped into the fluidic module, and output media from the fluidic module is delivered to the at least one sensing port.

In some embodiments, the fluidic device is configured such that each fluidic module is individually perfusable with its output media directed to the at least one sensing port without disturbing the flow of the others.

In some embodiments, the fluidic module comprises a bioreactor, chemostats, wells, an organ-on-chip, or a combination of them.

In some embodiments, the fluidic chip has a body in which the fluidic network is formed, and a fluidic chip registration means formed on the body for aligning the fluidic chip with a support structure.

In some embodiments, the fluidic chip registration means is configured such that multiple fluidic chip orientations are allowed while maintaining automatic and precise mechanical alignment to the support structure.

In some embodiments, the fluidic chip is configured such that one or more plug-in accessories are addable in or removable from the fluidic chip.

In some embodiments, the fluidic chip is formed of an elastic material such that compression of the actuator on the body causes at least one of the channels to be occluded.

In some embodiments, the fluidic network further comprises a first fluidic bus and a second fluidic bus, and wherein each channel module is connected between the first fluidic bus and the second fluidic bus.

In some embodiments, each channel module has an intermediate channel connected between the first fluidic bus and the second fluidic bus; a first channel connected to the intermediate channel at a first position and one of the pair of input ports; and a second channel connected to the intermediate channel at a second position and the other of the pair of input ports, wherein the first position is between the first fluidic bus and the second position, and the second position is between the first position and the second fluidic bus.

In some embodiments, the actuator comprises a plurality of actuating elements disposed on the body of the fluidic chip, such that compression of an actuating element on the body causes fluidic flow through a corresponding channel portion at which said actuating element is located to be occluded, wherein each of three actuating elements of the plurality of actuating elements are over the intermediate channel of a respective channel module at first, second and third locations in first, second and third channel portions of the intermediate channel, respectively, wherein the first channel portion is between the first fluidic bus and the first position, the second channel portion is between the second position and the second fluidic bus, and the third channel portion is between the first and second positions.

In some embodiments, the actuator further comprises an actuator head for selectively compressing or relaxing each of the plurality of actuating elements.

In some embodiments, the actuator head comprises an outer relief for controlling access to the at least one sensing port, an inner relief for controlling access to the at least one make-up media port, and a middle relief pocket having two ends and a gap defined therebetween.

In some embodiments, when the outer relief, the inner relief, and the gap are misaligned with any channel module, all of the first and second actuating elements are pressed by the surface of the actuator head, while all of the third actuating elements are relaxed by the middle relief pocket, so that each channel module is in the run mode. When the outer relief, the inner relief, and the gap are aligned with the intermediate channel of a channel module, the first and second actuating elements on said channel module are relaxed by the first and second reliefs, respectively, and the third actuating element on said channel module is pressed by the gap, all of the first and second actuating elements on the other channel modules are pressed by the surface of the actuator head, while all of the third actuating elements on the other channel modules are relaxed by the middle relief pocket, so that said channel module is in the analysis mode and all of the other channel modules are in the run mode.

In some embodiments, a rotation of the actuator head at a predetermined angle selects which channel module is in the analysis mode.

In some embodiments, replacement fluid can be injected into the output line of the isolated module without disturbing the flows of the other fluidic modules.

In some embodiments, the fluidic network further comprises one or more additional ports for flushing the first fluidic bus and/or the second fluidic bus.

In some embodiments, the fluidic device is a direct-access valve or a random-access valve.

To further illustrate the principles of the invention and their practical applications, certain exemplary embodiments of the invention are described below with reference to the accompanying drawings.

In certain embodiments, the multichannel microfluidic valves enable efficient scaling of the perfusion systems depicted in FIGS. 1A-1F. Each of the valve configurations is comprised of a network of fluidic microchannels within a deformable, elastomeric polymer or similar material. Rigid actuating elements superimposed upon certain critical regions of the network(s), when displaced by an actuator, either pinch the region closed and block passage of fluid therethrough, or relax, thereby allowing the channel to open and permitting fluid to pass. The valves are connected to external constructs (pumps, reservoirs, sensors) via tubing or other conduits attached to integrated ports.

Perfusate circulation within the systems of FIG. 1A-1F may be gravity-driven, as shown in FIGS. 1A, 1B, and 1E, or may be actively accomplished using pumps, as shown in FIGS. 1C, 1D, and 1F. The pumps can be a single-channel spiral pump 710 shown in FIG. 7A according to one embodiment of the invention, which includes a single spiral channel 711. With recirculation, media flows continuously through the circuit (the single spiral channel 711) at whatever rate is required to recapitulate a physiological residence time in each fluidic model. For pumped rather than gravity perfusion of a two-chamber bioreactor 118 shown in FIG. 1B, a two-channel pump 720 shown in FIG. 7B can be used, according to one embodiment of the invention, which includes two spiral channels 721 and 722.

Figure 7C:
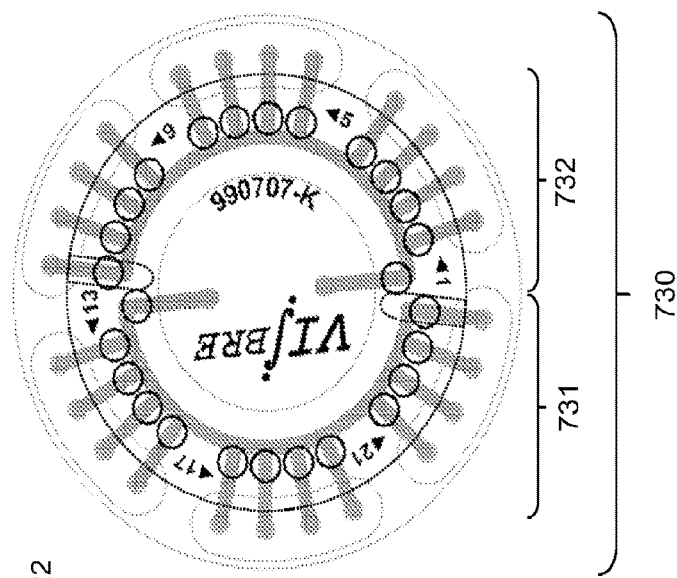
FIGS. 7A-7C show schematically different implementations of a pump, according to embodiments of the invention.
Figure 7B:
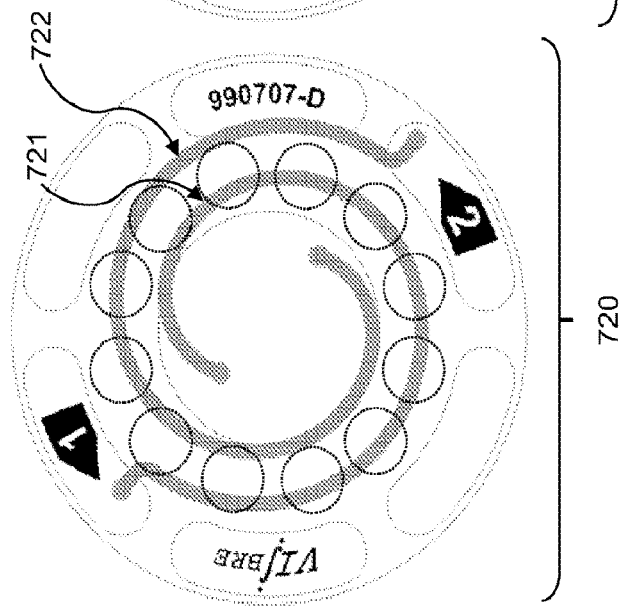
Figure 7A:
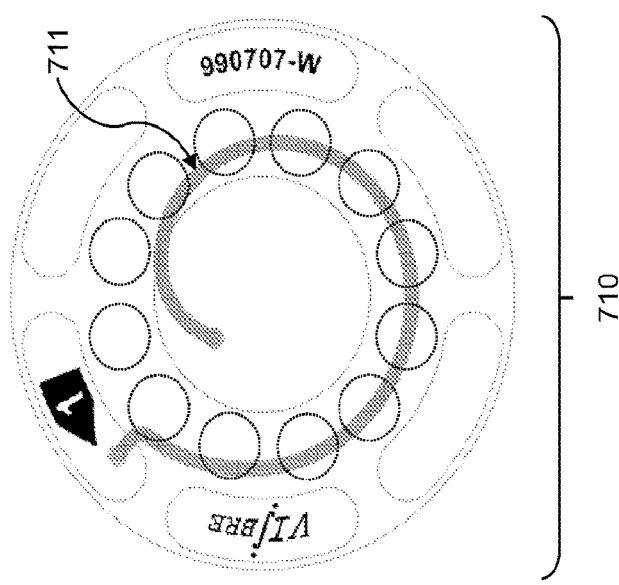

Just as FIG. 3B shows a 25-channel valve that can be used to deliver a selected media or drug to a bioreactor or chemostat, a single 2×12-channel perfusion/collection valve 730 shown in FIG. 7C according to one embodiment of the invention may be employed to deliver media to each side of a two-chambered bioreactor, or N=2 in FIG. 1E or 1F, or to the upstream and downstream ports of a single bioreactor. In another embodiment, this valve's integrated channel network is divided into two ganged halves 731 and 732, with 12 outlet ports upstream from N=12 bioreactors, and 12 downstream collection ports as shown for a single bioreactor shown in FIG. 1C. The downstream network 731 collects the media that perfuses each of the 12 bioreactors and is collected in N reservoirs 117, and with a single, time-shared pump 130 returns the media to the appropriate supply reservoir 106, which also serves to control media oxygenation. The channels within this valve 730 are opened in port-pairs; that is, for example, Port 5 would be connected to the outlet port via its corresponding common channel at the same time that Port 17 is opened to the collection port via its respective common channel. Similarly, Ports 12 and 24 are activated concurrently, as shown in FIG. 7C, and so on. For any given active port-pair, the remaining ports are closed to flow, and the connected modules would see no net movement of fluid therethrough. The configuration of the valve 730 enables time-division multiplexing to control the relative perfusion of each of N≤12 modules. In one embodiment shown in FIG. 7C, the 13th port in the valve can be used to flush the common channel if desired. When used for media-replacement, the two-channel spiral pump 720 shown in FIG. 7B ensures that whatever volume of media is withdrawn from a chamber for sampling is made up with media withdrawn from a replacement reservoir. Not shown, a 1×25 port valve at the output of any pump could direct the sample to any well in a 24-well plate, with the 25th port being used to flush the pump and valve to prevent mixing of samples from different chambers.

Figure 8A:
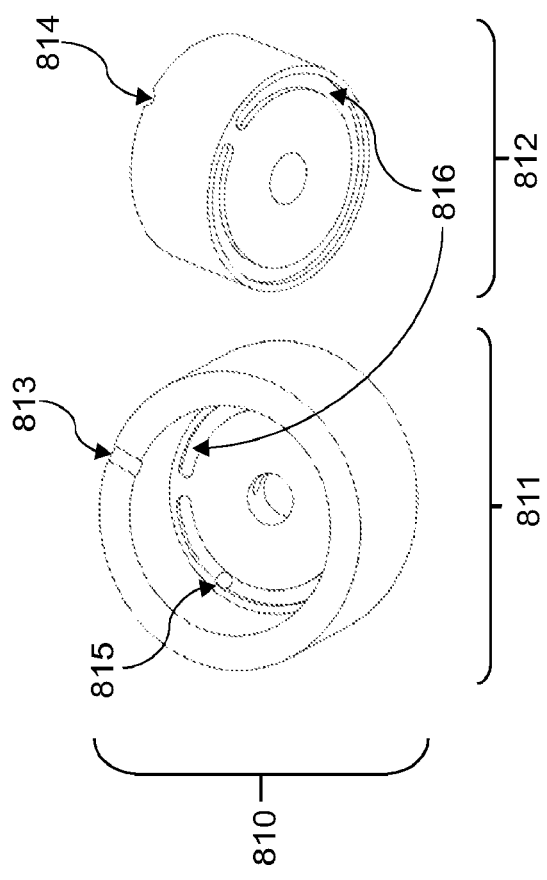
FIGS. 8A-8C show schematically a universal valve, according to embodiments of the invention.
Figure 8B:
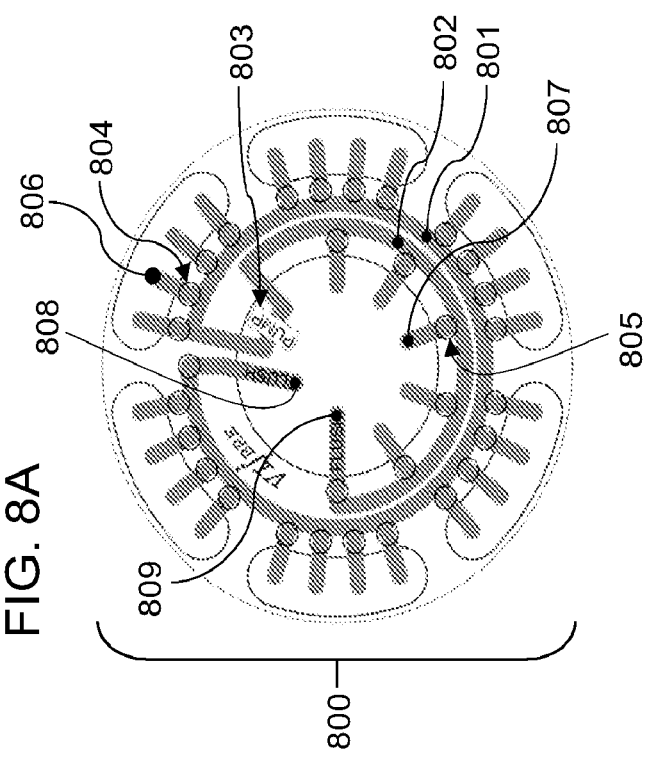
Figure 8C:
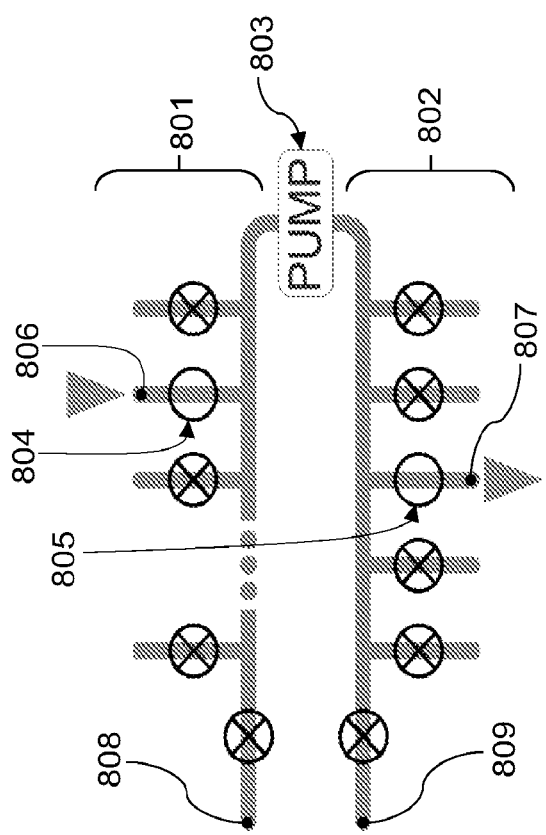

FIGS. 8A-8C show a universal valve chip 800 as used with a lagging actuator assembly 810, a combination which allows independent selection of both collection source and destination sink using a single valve construct with a single motor, according to embodiments of the invention. Two fluidic buses (common channels) 801 and 802 are connected by an offboard pump 803. Alternatively, if passive gravity-driven flow is desired, or if individual pumps are to be used inline either upstream or downstream of the valve chip 800, a shunt (not shown) may be installed in lieu of the pump 803. A schematic diagram of the fluidic control network shown in FIG. 8A is clarified by FIG. 8C.

Depending on the direction in which the pump 803 is operating, either bus 801/802 may serve as a collection conduit or an output conduit, while the other bus 802/801 serves as output or collection, respectively. In the exemplary embodiment shown in FIG. 8C, where the arrows indicate fluid flow, the bus 801 is the collection conduit and the bus 802 is the output conduit, but these could be switched. Ports 808 and 809 may serve as flush ports to clear common channels (buses) 801 and 802, or may be used as additional analysis ports. Additional ports and corresponding connecting channels may be added to (or removed from) the buses 801 and 802.

The lagging actuator assembly 810, as shown in FIG. 8B, functions similarly to the lagging actuator assembly 610 shown in FIG. 6B, and is used to select one collection port 806 and one output port 807. This is accomplished when the actuator groove 813 in the driving actuator 811 aligns with the actuating element 804, and the actuating groove 814 in the driven actuator 812 aligns with the actuating element 805. When the grooves 813 and 814 align with the actuating elements 804 and 805, respectively, those actuating elements 804 and 805 relax, and the corresponding port 806/807 is connected to the common channel of its respective bus 801/802, and thereby selected ports 806 and 807 become connected to each other. In this embodiment, one actuating element 804/805 in each bus 801/802 opens while all other actuating elements remain pressed into their corresponding regions, and those channels remain pinched closed.

In the present embodiment, the lagging actuator 810 has ample backlash such that any permutation of port-pair interconnections can be achieved. This backlash is accomplished by circular-segment pockets 816 with a near-360° sweep, and a single limiting ball 815, whose motion is constrained by the pockets 816, allowing the driving actuator 811 and the driven actuator 812 to rotate or remain stationary independently until the limiting ball 815 contacts opposing ends of both pockets 816, at which point both actuator parts 811 and 812 rotate as one. When the direction of the driving motor is then reversed, the motion of each actuator 811/812 becomes independent again. The sum of the pocket arc-lengths equals the backlash of the actuator assembly (not accounting for ball diameter).

In the embodiment shown in FIG. 8B, the outer actuator 811 is the driving actuator, and time-division multiplexing of solution in conduits attached to the outer bus 801 may be readily achieved, as described previously. In other embodiments, the driving actuator and the driven actuator may manifest such that the inner actuator 812 drives the outer actuator 811. By this means, time-division multiplexing may be readily achieved on the inner fluidic bus 802.

In additional embodiments of this invention, the actuator assembly concept may be extrapolated to include more than the two actuating "rings," which would address additional fluidic buses. The mechanical function of such embodiments would operate similar to the combination lock mechanism on an old-fashioned safe; that is, the primary actuator would drive the secondary actuator, which in turn would drive subsequent subordinate actuators in a cascading fashion.

Figure 9D:
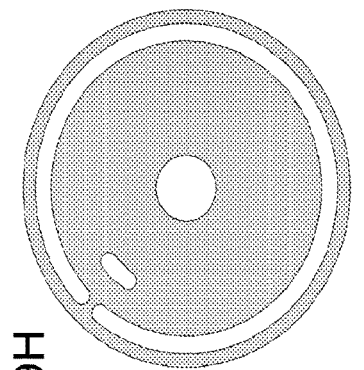

FIGS. 9A-9J provide details of a sensing valve assembly 920 according to embodiments of the invention, in which the fluidic chip 900 collects fluid from multiple (N≤24 as shown) inputs via ports such as 903 and 906, and directs either all of its inputs to a common output port 908, or all but a single selected input 906 to a common output 908, while fluid entering outlier port 906 is directed to an isolated "sensing" output 909, to which an analytical instrument is connected, as 221 shown in FIG. 2C. As in other valve assemblies previously discussed, the face of the actuator 910 presses the plurality of actuating elements 904 and 905 into the underlying elastomeric polymer, thereby pinching the corresponding channel closed, except in the regions where the outer relief pocket 913 has all outer actuating elements 904 relaxed, and where the inner actuating relief 914 has the inner actuators 905 relaxed. When the gap 915 in the outer relief pocket 913 aligns with an outer actuating element 904, that element closes the connection of the port at that location to the outer fluidic bus, i.e., a first common channel, 901 and hence a common output port 908, while the inner relief 914 at that angle allows that inner actuating element 905 to relax, thereby connecting the port at that angle to the inner fluidic bus, i.e., a second common channel, 902 and hence a sensing port 909. Hence, rotation of the actuator 910 selects which port is connected to the sensing port 909 and ensures that all of the other ports are connected to the common output port 908. As shown in FIG. 9A, in addition to the first common channel 901 and the second common channel 902, the channel network of the fluidic chip 900 also includes a plurality of intermediate channels 907. Each intermediate channel 907 is in fluidic communication with one input port 903 (or 906) and connected to the first common channel 901 and the second common channel 902.

The bioreactor media line that is to be analyzed is selected by rotating the actuator 910 to a position in which the actuating elements 904 and 905 corresponding to the selected target port 906 are switched such that the selected target port 906 becomes isolated from the common output 908 and opened to the sensing output 909, as exemplified in FIG. 9A. Meanwhile, all of the other ports 903 remain connected to the common output port 908 and isolated from the sensing port 909. As shown in FIG. 9C, the actuating elements 904 and 905 are constrained by a cage 921, and the fluidic chip 900 is constrained by a baseplate 922.

Figure 9E:
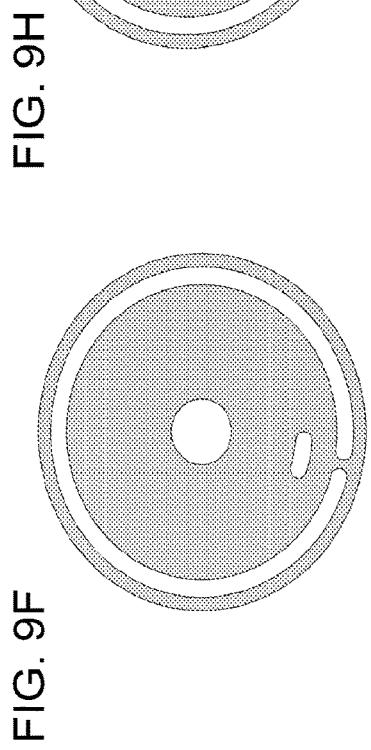
Figure 9F:
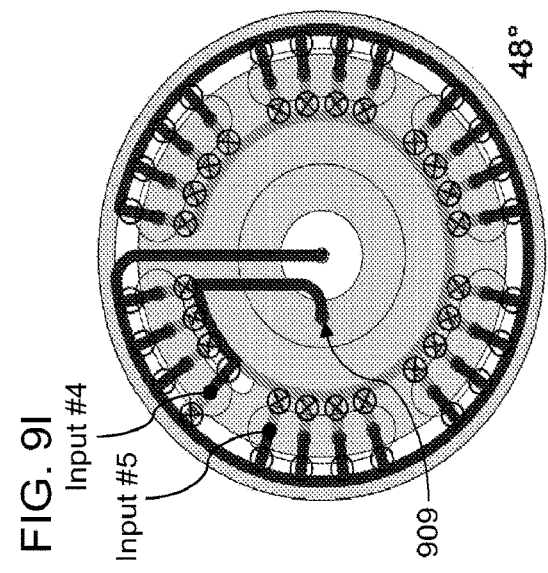
Figure 9G:
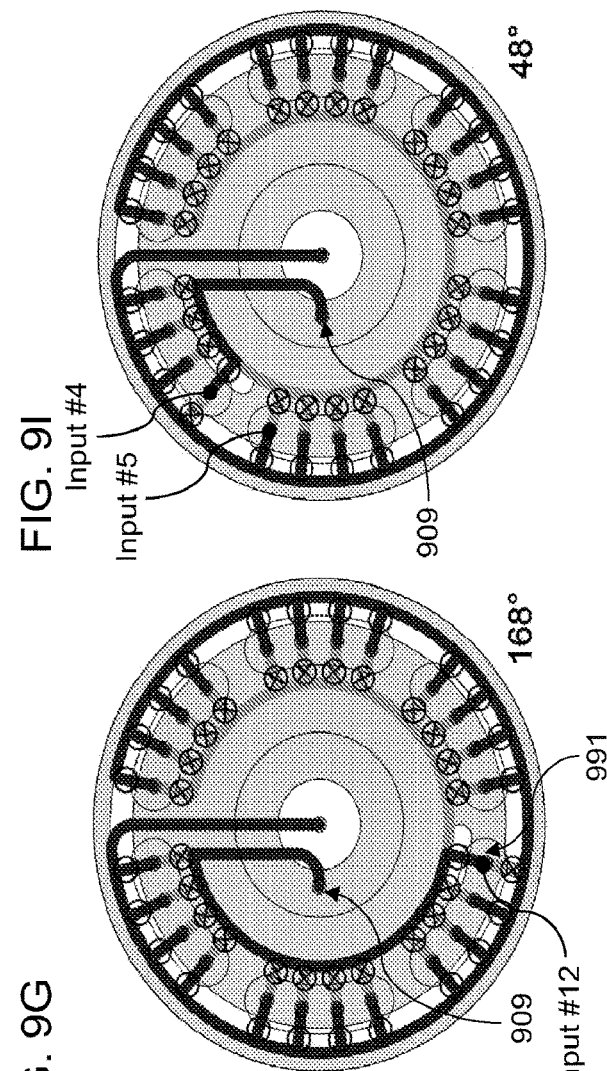
Figure 9H:
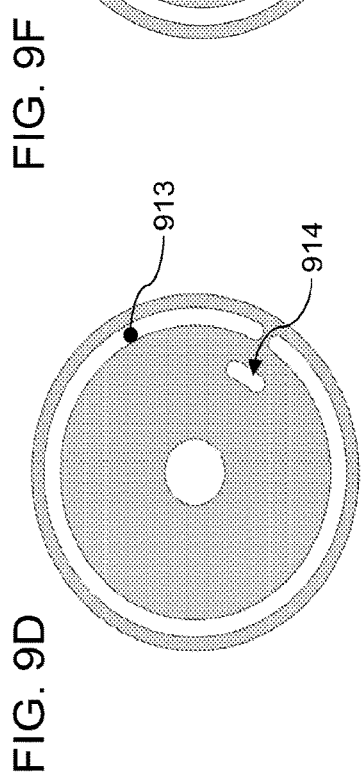
Figure 9I:
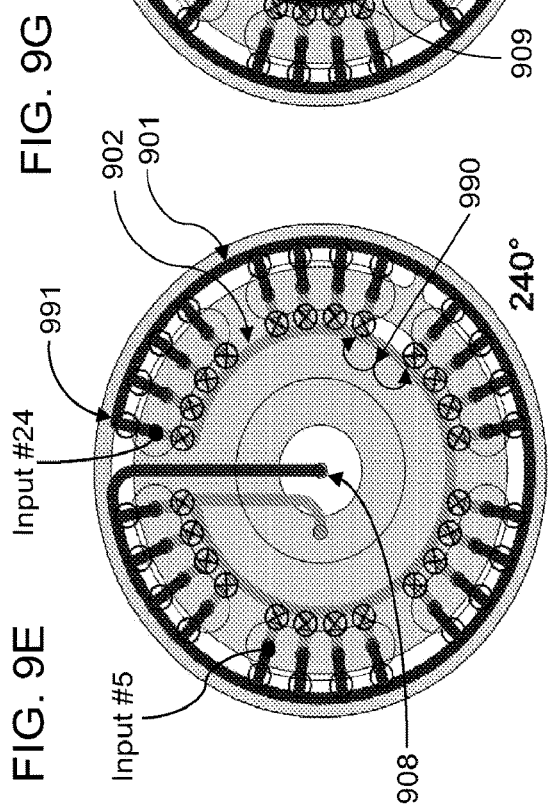
Figure 9J:
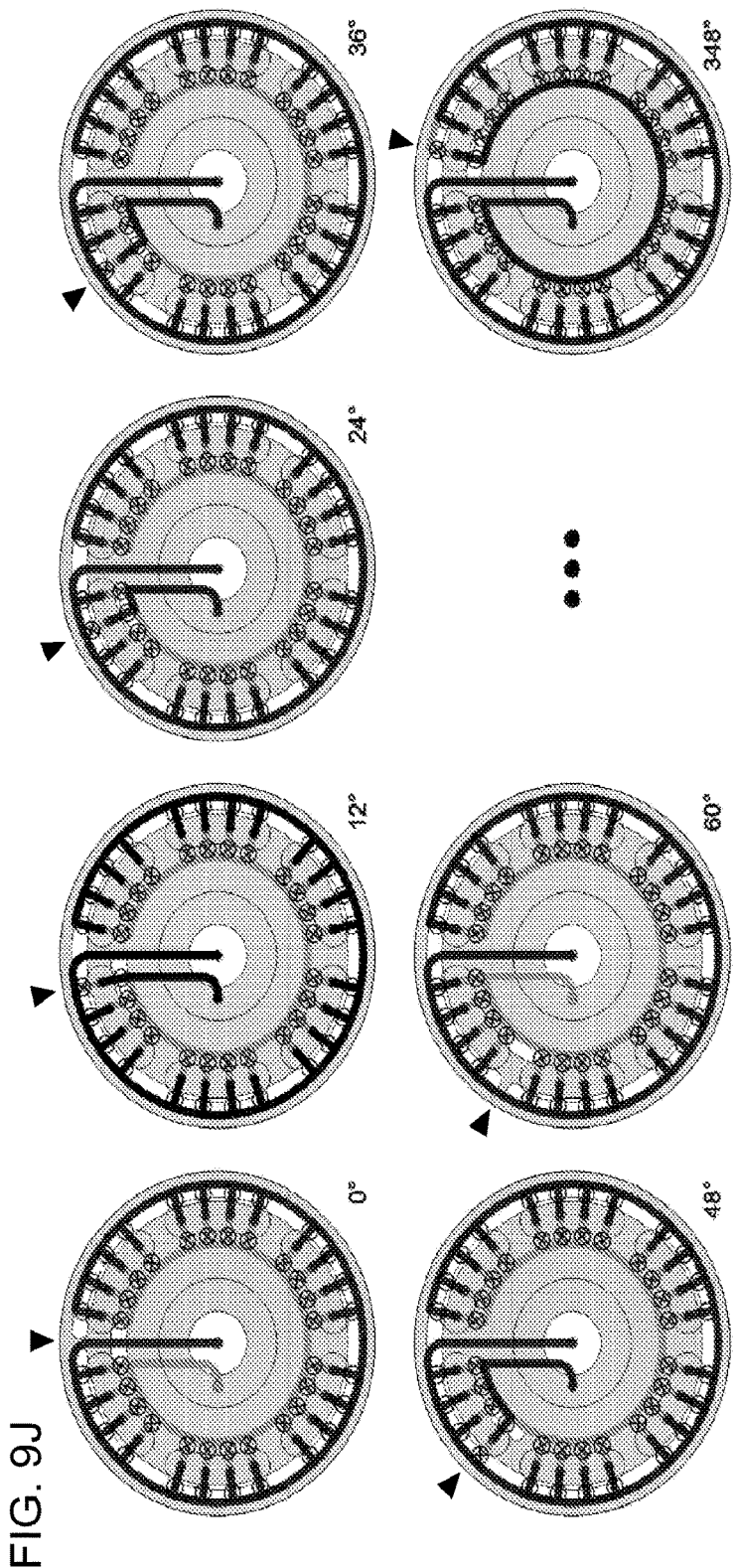

As a further example of the function of the valve 900, FIGS. 9D-9I show the actuator position (FIGS. 9D, 9F and 9H) and the channel and port status (FIGS. 9E, 9G and 9I) for three actuator positions (240°, 168°, and 48°). Referring to FIGS. 9D and 9E, the position of the inner relief 914 is such that the two inner actuating elements 990 at positions 16 and 17 remain compressed, and all of the outer actuating elements 904 are relaxed, so that all ports are connected to the common channel 901. In FIGS. 9F and 9G, input #12 (991) is connected to the sensing/analysis port 909 because the inner actuating element 905 at that position is relaxed while the corresponding outer one 904 is compressed. Similarly, in FIGS. 9H and 9I, input #4 is connected to the analysis port 909, from which all other inputs are isolated. FIG. 9J shows sequential connection and disconnection of adjacent ports can be accomplished by the rotation of the actuator 910 in increments of 12°. Note that while this valve allows a single bioreactor to be sampled at a given time, it also prevents any backpressure on the organs not being sampled, as their perfusate is directed towards waste rather than being blocked, which could increase the pressure in the reactor.

Figure 10:
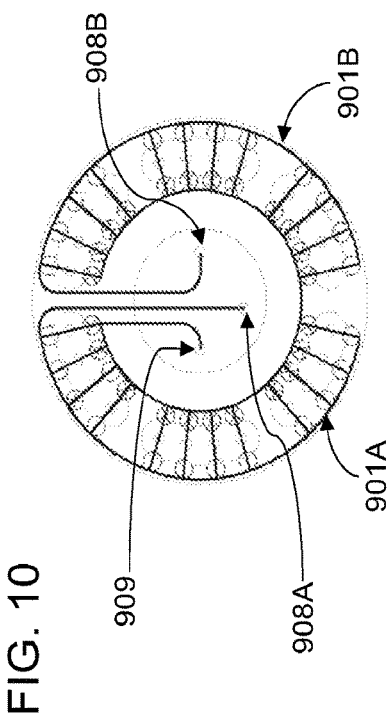
FIG. 10 shows schematically an alternative sensing valve, according to embodiments of the invention.

FIG. 10 shows a minor modification of the valve 900, wherein the outer fluidic bus is divided into two separate sections 901A and 901B, each of which is connected to a respective common output 908A or 908B. This allows some of the channels to have a different normal common channel so that the outputs do not have to mix from every channel. Such modification allows one to send solutions to the analytical line 909 (calibration solutions) that should not get mixed with the solution going to the other (organ) channels.

FIGS. 11A-11M show a "cut-in" or "insert" valve according to embodiments of the invention.

Figure 11A:
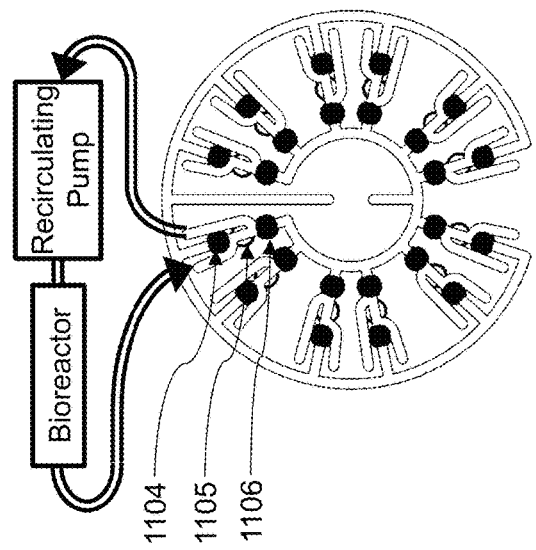
Figure 11C:
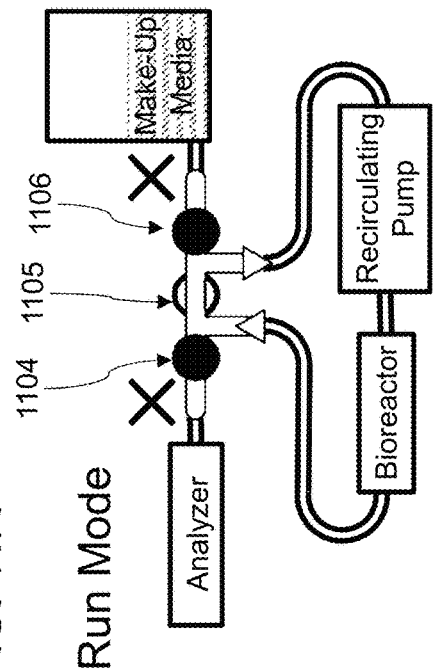
Figure 11B:
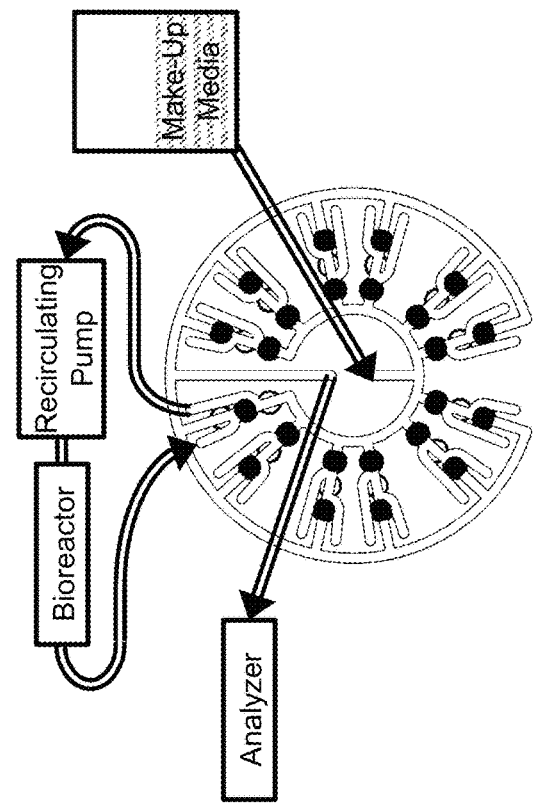

FIGS. 11A and 11B explain the concept of the "cut-in" or "insert" valve that supports a run mode in which a bioreactor is connected to a recirculating pump, and an analysis mode in which make-up media is pumped into the bioreactor, displacing media that is delivered to an analyzer, as discussed above for FIG. 2D. For each module of the valve, there are four connections and three actuating elements. In the run mode seen in FIG. 11A, the actuating element 1105 is relaxed so that the recirculating pump can push media through the bioreactor, while the actuating elements 1104 and 1106 compress their corresponding channels, thereby isolating this bioreactor-pump module from both the analyzer and the media supply. In the analysis mode, the actuating element 1105 is in compression and the actuating elements 1104 and 1106 are relaxed, thereby allowing the make-up media to be drawn from its reservoir and the bioreactor effluent delivered to the analyzer, as shown in FIG. 11B.

Figure 11D:
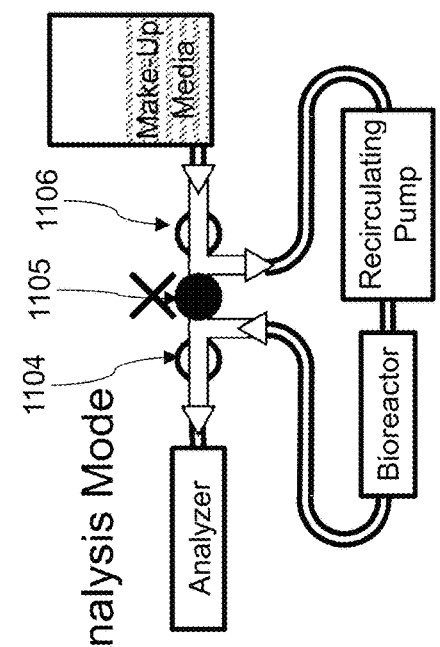
Figure 11H:
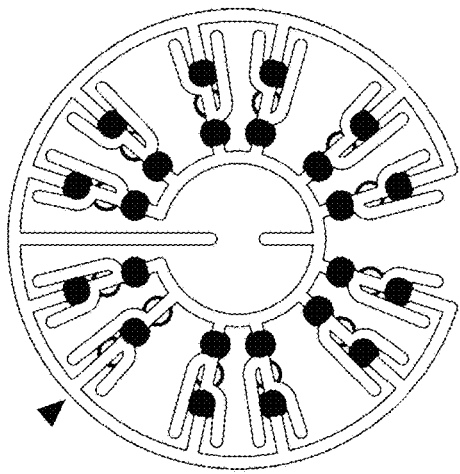
Figure 11J:
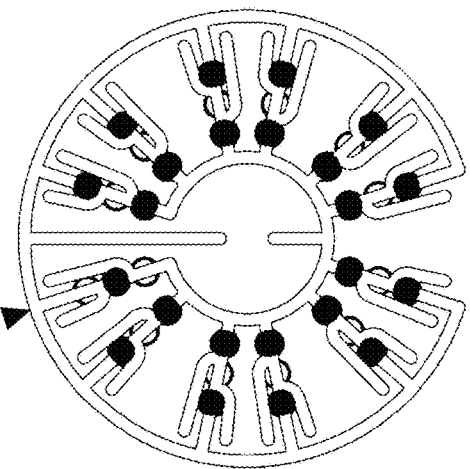
Figure 11L:
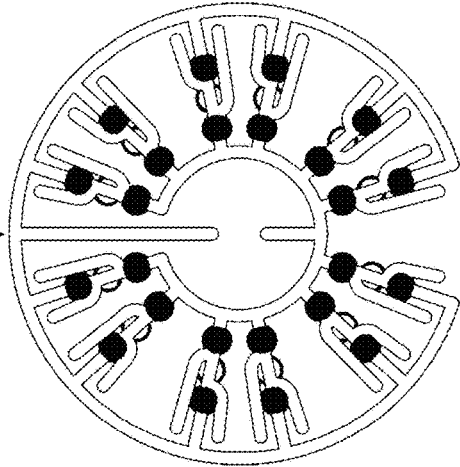
Figure 11I:
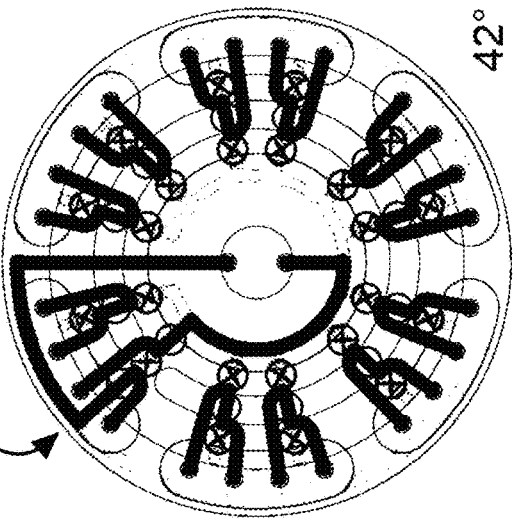
Figure 11K:
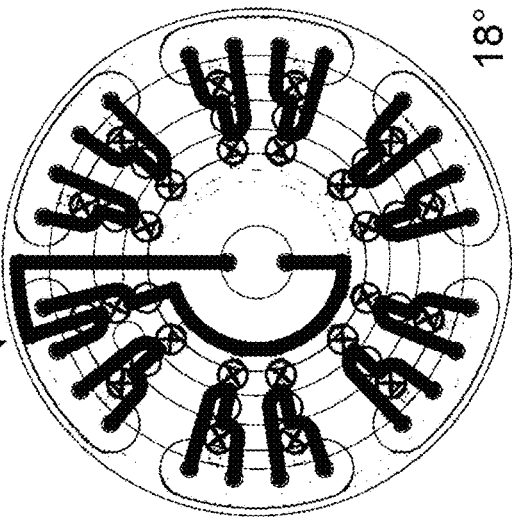
Figure 11M:
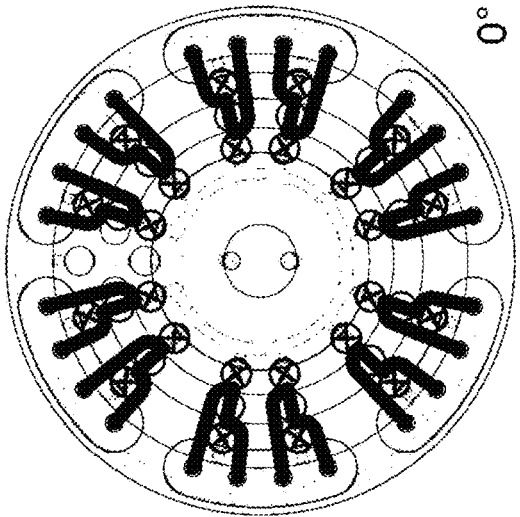
Figure 13A:
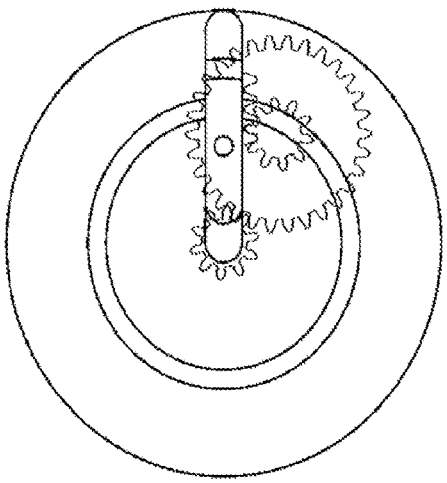
FIGS. 13A-13D show schematically a random-access cut-in valve, according to embodiments of the invention.
Figure 13B:
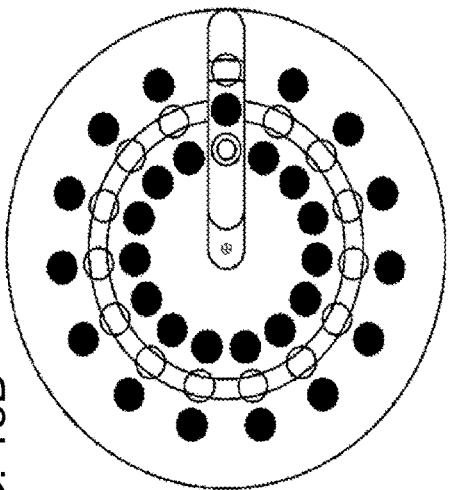
Figure 13C:
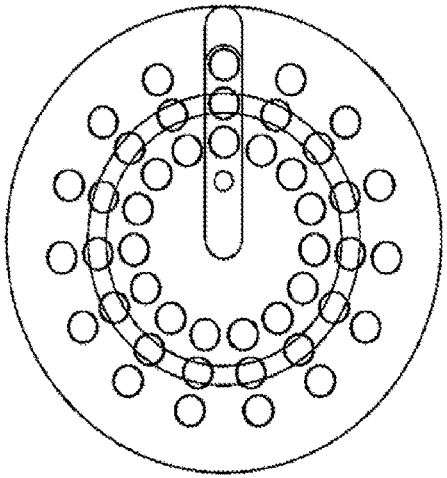
Figure 13D:
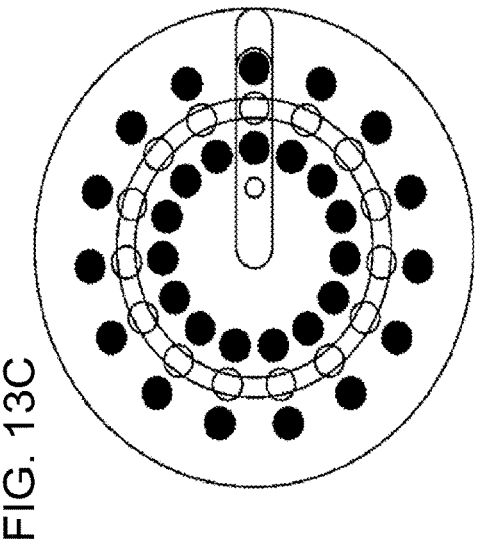

FIGS. 11C and 11D show the through-plate fluidic channel layout 1100 along with the actuating elements 1104-1106 that accomplish these modes for a total of 12 bioreactors. A rotation of the actuator by the appropriate angle allows the sequential sampling of each bioreactor. The topology enables serial access, and the valve has a low dead volume in each fluidic module loop. The majority of this valve's dead volume is in the analytical loop, and the clearing of that dead volume is limited by the amount of fresh media that can be added to sweep the analytical loop. In other embodiments, an extra input port uses fresh media to flush the channels.

FIG. 11E provides details of the actuating recesses of the actuator 1110, with an inner actuating relief 1114 controlling access to the media reservoir, an outer actuating relief 1116 controlling access to the analyzer, and the combination of a recess 1113 and a gap 1115 controlling the recirculation or isolation of the two halves of the circuit.

FIG. 11F shows the channel layout of the fluidic chip 1100 including a plurality of channel modules 1130, each channel module 1130 being in fluidic communication with a pair of input ports 1137 and 1138. An outer fluidic bus, i.e., a first common channel, 1133 is connected to an analyzer port 1134. An inner fluidic bus, i.e., a second common channel, 1135 is connected to a make-up media port 1136. The input to the recirculating pump is connected to a port 1137, while the return from the bioreactor is connected to a port 1138. As shown in FIG. 11F, each channel module 1130 includes an intermediate channel 1131 connected between the first common channel 1133 and the second common channel 1135; a first channel 1132a connected to the intermediate channel 1131 at a first position 1131a and the port 1138; and a second channel 1132b connected to the intermediate channel 1131 at a second position 1131b and the port 1137.

The first position 1131a is between the first common channel 1133 and the second position 1131b, and the second position 1131b is between the first position 1131a and the second common channel 1135.

FIG. 11G provides details of the cut-in valve subassembly 1120, in which the fluidic chip 1100 interfaces with multiple (N≤12 as shown) bioreactors via ports 1137 and 1138 shown in FIG. 11F. As in other valve assemblies previously discussed, the face of an actuator 1110 presses the plurality of the outer, middle, and inner actuating elements 1104, 1105, and 1106, respectively, into the underlying elastomeric polymer (fluidic chip) 1100, thereby pinching the corresponding channels closed, except in the regions where the middle relief pocket 1113 has all of the middle actuating elements 1105 relaxed; where the inner actuating relief 1114 has an inner actuator 1106 relaxed; and the outer actuating relief 1116 has an outer actuating element 1104 relaxed. When the gap 1115 in the middle relief pocket 1113 aligns with a middle actuating element such as 1105, that element closes the connection of the port at that location to block recirculation of that module. At the same time for that angular position, the outer actuating element 1104 is relaxed so that the outer fluidic bus 1133 and hence the analyzer port 1134 are connected to that bioreactor, while the inner actuating element 1106 is relaxed and the make-up media port 1136 is connected to the inner fluidic bus 1135 and hence the output of the bioreactor. Hence, rotation of the actuator 1110 selects which bioreactors are recirculating, and which one is connected to both the make-up media and the analyzer. While one bioreactor is being analyzed, all others are recirculating independently, as shown in FIG. 2D.

The bioreactor media line that is to be analyzed is selected by rotating the actuator 1110 to a position in which the actuating elements 1104 and 1106, corresponding to the selected bioreactor target port, are switched open, and the actuating element 1105 is closed, such that the make-up media enters the valve through port 1136, and by means of the recirculating pump displaces media from the selected bioreactor that is then pushed out through the analysis port 1134. As shown in FIG. 11G, the actuating elements 1104, 1105, and 1106 are constrained by the cage 1121, and the fluidic chip 1100 is constrained by the baseplate 1122.

As a further example of the function of the valve 1120, FIGS. 11H-11M show the actuating element position (FIGS. 11H, 11J, and 11L) with black dots as closed and clear-center as open, and the corresponding channel and port status (FIGS. 11I, 11K, and 11M) for three actuator positions (0°, 18°, and 42°). At 0°, all bioreactors are in a run mode, while a rotation of 18° puts one bioreactor into an analyze mode, and a subsequent rotation to 42° does that for the next bioreactor. Note that while this valve allows a single bioreactor to be sampled at a time, it also prevents any backpressure on the bioreactors not being sampled, as their perfusate is recirculated rather than being blocked, which could alter the pressure in the bioreactor.

Figure 12:
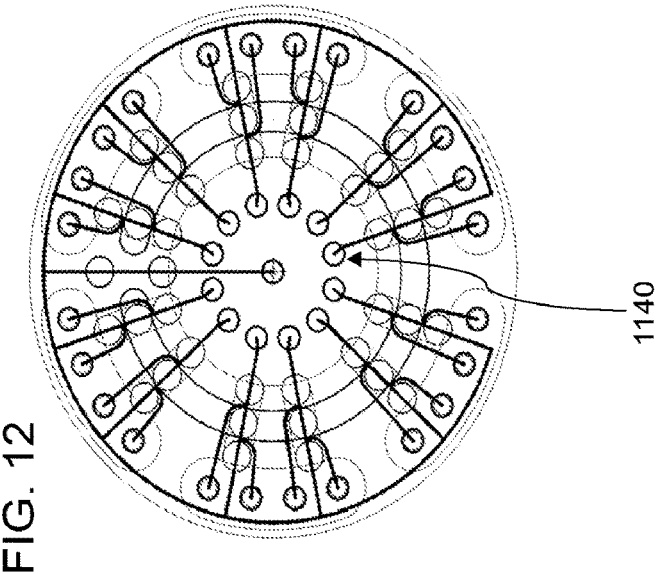
FIG. 12 shows schematically a cut-in valve with individual make-up inputs, according to embodiments of the invention.

FIG. 12 shows a modification of the valve network 1100, wherein the single make-up media port 1136 is divided into multiple media ports 1140, each of which is connected to a respective fluidic module, which allows switched insertion of analytical devices or other fluidic modules into any fluid line and does not cause any cross contamination between sampled sites.

Among other things, the valve designs shown in FIGS. 11A-11M and 12 provide a great deal of advantages in controlling and sensing bioreactors, including chemostats and microchemostats. The valve allows switched insertion of analytical devices or other fluidic modules into any fluid line (currently designed for Tygon 0.060 O.D., but many other tubing sizes are possible) and does not cause cross contamination between sampled sites. This could allow a single analytical instrument to take measurements on isolated systems or take samples from different locations within a single system. Sampling sites are completely independent, which allows them to be arranged either on parallel legs of a perfusion system or in series between experimental points along a path or any desired combination.

Sampled devices are completely independent or may be arranged either in parallel or in series with each other or any desired combination.

The actuator design also allows easy configuration for a variety of ball position layouts and can accommodate valve designs for various motor sizes (the current design has a 24 mm diameter actuator that may be used with NEMA 8 motors). Actuation on the radial centerline makes scaling and reconfiguration simple.

Series measurements along an experimental path allow measurements of both inputs and outputs using a single instrument and allows direct comparisons of input fluid composition vs output fluid composition throughout an experimental sequence. The design simply breaks the fluid path and inserts the sampling loop, which could either be closed for recirculation (other fluidic devices or non-destructive analysis only, e.g., optical density, colorimetric pH, etc.) or connected to a fluid replenish reservoir to add fresh media to replace the volume extracted during sampling. With properly sized compression zones and fluidic channels, this design is zero dead volume in the normal flow loop.

Using an end-to-beginning sample sequence allows for fast sampling of each location within a series with destructive testing without cross contamination or the requirement to wait for analyte concentrations to return to normal after a fresh media injection (each new media injection happens downstream of the next measurement site).

Utilizing a separate set of analytical pumps and valves for washing and calibrating makes the organ/bioreactor system perfusion more reliable and completely independent of the analytical system's maintenance requirements.

The individual channel design allows easy configuration for a variety of channel numbers, which enables it to be used on various motor sizes without additional engineering time to redesign the fluidic channels. Utilizing the radial inline orientation of the compression balls allows this design to be used with the radial cylinder random-access actuator concept.

Although the valve provides isolation within its own design, it cannot provide any isolation for organs connected in parallel through external connections, and another valve would be required for that function.

In certain embodiments, the design principles of FIGS. 6A-6C and 8A-8C can be used to create a random-access cut-in valve, which is shown in FIGS. 13A-13D according to certain embodiments of the invention. Sequential operation is accomplished when running in the counterclockwise direction. Random-access operation is achieved by rotating in the clockwise direction by 216 degrees (120 steps on a standard stepper motor), then rotating to the desired position, and then by reversing back 216 degrees in the counterclockwise direction.

The valves disclosed herein can be implemented with the cartridge pumps and valves described in this disclosure and earlier patents, or with integrated fluidic chips also described in other patents. If desired, physiological flow pulsations can be provided by periodic changes in pump speed. These advances provide the necessary parallelism to sample with a common instrument various configurations of multiple organs-on-chips, tissue chips, bioreactors, or fluidic modules.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the invention pertains without departing from its spirit and scope. Accordingly, the scope of the invention is defined by the appended claims rather than the foregoing description and the exemplary embodiments described therein.

Some references, which may include patents, patent applications, and various publications, are cited and discussed in the description of the invention. The citation and/or discussion of such references is provided merely to clarify the description of the invention and is not an admission that any such reference is "prior art" to the invention described herein. All references cited and discussed in this specification are incorporated herein by reference in their entireties and to the same extent as if each reference was individually incorporated by reference.

REFERENCES

[1]. Esch, M B, et al., How multi-organ microdevices can help foster drug development. Adv. Drug Del. Rev., 69:158-169. 2014.

[2]. Abaci, H E, and Shuler, M L. Human-on-a-chip design strategies and principles for physiologically based pharmacokinetics/pharmacodynamics modeling. Integr. Biol., 7:383-391. 2015.

[3]. Wang, Y I, et al., Self-contained, low-cost Body-on-a-Chip systems for drug development. Exp. Biol. Med.: Accepted. 2017.

[4]. Maschmeyer, I, et al., A four-organ-chip for interconnected long-term co-culture of human intestine, liver, skin and kidney equivalents. Lab Chip, 15:2688-2699. 2015.

[5]. Edington, C D, et al., Interconnected Microphysiological Systems for Quantitative Biology and Pharmacology Studies. Sci. Rep., 8: 4530. 2018.

[6]. Wikswo, J P, et al., Scaling and systems biology for integrating multiple organs-on-a-chip. Lab Chip, 13:3496-3511. 2013.

[7]. Darby, S, et al., A metering rotary nanopump for microfluidic systems. Lab Chip, 10:3218-3226. 2010. PMCID: PMC4156019.

[8]. Wikswo, J P, et al., Engineering Challenges for Instrumenting and Controlling Integrated Organ-on-Chip Systems. IEEE Trans. Biomed. Eng., 60:682-690. 2013. PMCID: PMC3696887.

[9]. Block I I I, F E, Samson, P C, and Wikswo, J P, "Normally closed microvalve and applications of the same", U.S. Pat. No. 9,618,129 B2 (Apr. 11, 2017).

[10]. Markov, D A, Manuel, S, Shor, L, Opalenik, S R, Wikswo, J P, and Samson, P C. Tape underlayment rotary-node (TURN) valves for simple on-chip microfluidic flow control. Biomed. Microdevices, 12:135-144. 2010.

[11]. LeDuc, P R, Messner, W C, and Wikswo, J P. How do control-based approaches enter into biology? Annu. Rev. Biomed. Eng., 13:369-396. 2011.

[12]. Cyr, K J, Avaldi, O M, and Wikswo, J P. Circadian hormone control in a human-on-a-chip: In vitro biology's ignored component? Exp. Biol. Med., 242:1714-1731. 2017. PMCID: PMC5832251.

[13]. Wolcott, D K, and Marshall, G D, "Pulseless, reversible precision piston-array pump", U.S. Pat. No. 6,079,313 (27 Jun. 2000).

[14]. Block I I I, F E, et al., "Organ on chip integration and applications of the same", U.S. Pat. No. 9,874,285 B2 (Jan. 23, 2018).

[15]. Wikswo, J P, et al., "Integrated organ-on-chip systems and applications of the same," U.S. Pat. No. 10,078,075 B2 (Sep. 18, 2018).

[16]. Wikswo, J P, et al., "Integrated Organ-on-Chip Systems and Applications of the Same", U.S. Pat. No. 10,444,223 B2 (Oct. 15, 2019).

[17]. Wikswo, J P, Markov, D A, and Reiserer, R S, "Multicompartment Layered and Stackable Microfluidic bioreactors and Applications of same", U.S. Pat. No. 10,464,064 B1 (Nov. 5, 2019).

[18]. Gould, P A, et al., "Peristaltic micropump and related systems and methods", U.S. Pat. No. 10,487,819 B2 (Nov. 26, 2019).

[19]. Wikswo, J P, Markov, D A, and Reiserer, R S, "Multicompartment layered and stackable microfluidic bioreactors and applications of same", U.S. Pat. No. 10,532,354 B2 (Jan. 14, 2020).

[20]. NCATS Supports Award-Winning Technology for Drug Development: NIH; 2018 [updated Sep. 21, 2018. https://ncats.nih.gov/pubs/features/microformulator (accessed Jan. 2, 2019).

[21]. Wikswo, J P, et al., "Interconnections of multiple perfused engineered tissue constructs and microbioreactors, multi-microformulators and applications of the same," U.S. Pat. No. 10,023,832 B2 (Jul. 17, 2018).

[22]. Wikswo, J P, Reiserer, R S, and Hawkins, K, "System and method for microdialysis imaging and regional fluidic delivery and control and applications of same," U.S. Pat. No. 10,538,726 B2 (Jan. 21, 2020).

What is claimed is:

1. A fluidic device, comprising:
a fluidic chip having a body and a fluidic network formed in the body, the fluidic network comprising a plurality of fluidic channels in fluidic communication with a plurality of input ports, at least one output port, and at least one sensing port; and an actuator configured to engage with the fluidic network to control each fluidic channel to switch between an open state in which fluidic flow through said fluidic channel is permitted and a closed state in which no fluidic flow through said fluidic channel is permitted, so as to selectively collect fluid from multiple inputs via the plurality of input ports, and direct either all of the multiple inputs to the at least one output port, or all but a single selected input to the at least one output port and the single selected input to the at least one sensing port to which an analytical instrument is operably connected, wherein the plurality of input ports is operably coupled with a plurality of fluidic modules, wherein in operation, the plurality of fluidic modules is individually perfused, and outputs of all of the plurality of fluidic modules are directed to the at least one output port, or an output of any one of the plurality of fluidic modules is directed to the at least one sensing port, while outputs of all other fluidic modules of the plurality of fluidic modules are directed to the at least one output port, wherein the plurality of fluidic channels comprises a first common channel, a second common channel, and a plurality of intermediate channels, each intermediate channel being in fluidic communication with at least one of the plurality of input ports and connected to the first common channel and/or the second common channel, and wherein the actuator comprises
  a plurality of actuating elements disposed on the body of the fluidic chip with each actuating element at a location that is over an intermediate channel and is located between a respective port and one of the first common channel and the second common channel to which said intermediate channel is connected, wherein the plurality of actuating elements comprises caged actuating elements; and
  an actuator head having a cylinder shape configured to be rotatable over the plurality of actuating elements, and including one or more grooves, one or more reliefs, and/or one or more pockets operably engaging with the plurality of actuating elements for selectively compressing or relaxing each of the plurality of actuating elements, such that compression of said actuating element on the body causes fluidic flow between said respective port and said one of the first common channel and the second common channel through said intermediate channel to be occluded so that said intermediate channel is in the closed state, or relaxation of said actuating element on the body causes fluidic flow between said respective port and said one of the first common channel and the second common channel through said intermediate channel to flow so that said intermediate channel is in the open state; and
  wherein the fluidic chip has a circular shape adapted for engaging with the cylinder shaped actuator head.

2. The fluidic device of claim 1, wherein when said output of any one of the plurality of fluidic modules is directed to the analytical instrument, the outputs from all other fluidic modules of the plurality of fluidic modules flow without interruption.

3. The fluidic device of claim 1, wherein the plurality of fluidic modules comprises bioreactors, wells, organs-on-chips, chemostats, or a combination of them.

4. The fluidic device of claim 1, wherein the fluidic chip further has a fluidic chip registration means formed on the body for aligning the fluidic chip with a support structure.

5. The fluidic device of claim 4, wherein the fluidic chip registration means is configured such that multiple fluidic chip orientations are allowed while maintaining automatic and precise mechanical alignment to the support structure.

6. The fluidic device of claim 1, wherein the fluidic chip is formed of an elastic material such that compression of the actuator on the body causes at least one of the channels to be occluded.

7. The fluidic device of claim 1, wherein the locations of the plurality of actuating elements on the body of the fluidic chip comprise first locations and second locations, wherein the first locations comprise each actuating element location over a respective intermediate channel between a respective port and the first common channel, and the second locations comprise each actuating element location over a respective intermediate channel between a respective port and the second common channel.

8. The fluidic device of claim 7, wherein the actuator head comprises:
  an outer actuator head having an outer groove corresponding to one of the first locations of the plurality of actuating elements on the body, wherein the outer groove, when aligned with the corresponding one of the first locations, relieves the corresponding actuating element so that the corresponding port is connected to the first common channel; and
  an inner actuator head sleeved in the outer actuator head, having an inner groove corresponding to one of the second locations of the plurality of actuating elements on the body, wherein the inner groove, when aligned with the corresponding one of the second locations, relieves the corresponding actuating element so that the corresponding port is connected to the second common channel,
  wherein one of the outer actuator head and the inner actuator head is a driving actuator head driven by a motor, and the other of the outer actuator head and the inner actuator head is a driven actuator head driven by said driving actuator head.

9. The fluidic device of claim 8, wherein each of the outer actuator head and the inner actuator head has a circular-segment pocket with a near-360° sweep, wherein the actuator head further comprises a single limiting element, whose motion is constrained by the pockets, allowing the driving actuator head and the driven actuator head to rotate or remain stationary independently until the limiting element contacts opposing ends of both pockets, at which point both actuator heads rotate as one, wherein when the direction of the motor is then reversed, the motion of each of the actuator heads becomes independent again.

10. The fluidic device of claim 7, wherein the actuator head comprises a first relief pocket having two ends and a gap defined therebetween, and a second relief aligned with the gap along an intermediate channel, wherein the first relief pocket and the gap are corresponding to the first locations of the plurality of actuating elements on the body of the fluidic chip, and the second relief is corresponding to one of the second locations of the plurality of actuating elements on the body of the fluidic chip, such that in operation, one of the actuating elements on the first locations is pressed by the gap and the others of the actuating elements on the first locations are relaxed by the first pocket, and one of the actuating elements on the second locations is relaxed by the second relief and the others of the actuating elements on the second locations are pressed by the surface of the actuator head, thereby directing the single selected input from the input port connected to said intermediate channel with which the gap and the second relief are aligned to the at least one sensing port through the second common channel, while directing the inputs from all of the other input ports to the at least one output port through the first common channel.

11. The fluidic device of claim 10, wherein a rotation of the actuator head at a predetermined angle selects which port is connected to the at least one sensing port, and ensures that all of the other ports are connected to the at least one output port.

12. The fluidic device of claim 10, wherein the first common channel comprises two separate sections, each of which is connected to a respective common output port, thereby allowing some of the fluidic channels to have a different common output port so that the inputs from the input ports do not have to mix from every channel.

13. The fluidic device of claim 1, wherein the fluidic network further comprises one or more additional ports for flushing the first common channel and/or the second common channel.

14. A fluidic device, comprising:
a fluidic chip having a body and a fluidic network formed in the body, the fluidic network comprising a plurality of channel modules, each channel module being in fluidic communication with a pair of input ports, at least one make-up media port, and at least one sensing port; and
an actuator configured to engage with the fluidic network to control each channel module to switch between a run mode in which the pair of input ports is fluidically connected to each other, and an analysis mode in which one of the pair of input ports is fluidically connected to the at least one make-up media port, while the other of the pair of input ports is fluidically connected to the at least one sensing port to which an analytical instrument is operably connected,
wherein the pair of ports of each channel module is operably coupled with a fluidic module and a recirculating pump, such that when said channel module is in the run mode, the fluidic module is fluidically connected to the recirculating pump in a circulating loop, and when said channel module is in the run mode, make-up media from the at least one make-up media port is pumped into the fluidic module, and output media from the fluidic module is delivered to the at least one sensing port,
wherein the actuator comprises
a plurality of actuating elements disposed on the body of the fluidic chip,
wherein the plurality of actuating elements comprises caged actuating elements; and
an actuator head having a cylinder shape configured to be rotatable over the plurality of actuating elements, and including one or more grooves, one or more reliefs, and/or one or more pockets operably engaging with the plurality of actuating elements for selectively compressing or relaxing each of the plurality of actuating elements, such that compression of an actuating element on the body causes no fluidic flow through a corresponding channel portion at which said actuating element is located, or relaxation of an actuating element on the body causes fluidic flow through a corresponding channel portion at which said actuating element is located; and
wherein the fluidic chip has a circular shape adapted for engaging with the cylinder shaped actuator head.

15. The fluidic device of claim 14, wherein the fluidic device is configured such that each fluidic module is individually perfusable with its output media directed to the at least one sensing port without disturbing the flow of the others.

16. The fluidic device of claim 14, wherein the fluidic module comprises a bioreactor, wells, an organ-on-chip, chemostat, or a combination of them.

17. The fluidic device of claim 14, wherein the fluidic chip further has a fluidic chip registration means formed on the body for aligning the fluidic chip with a support structure.

18. The fluidic device of claim 17, wherein the fluidic chip registration means is configured such that multiple fluidic chip orientations are allowed while maintaining automatic and precise mechanical alignment to the support structure.

19. The fluidic device of claim 14, wherein the fluidic chip is formed of an elastic material such that compression of the actuator on the body causes at least one of the channels to be occluded.

20. The fluidic device of claim 14, wherein the fluidic network further comprises a first common channel and a second common channel, and wherein each channel module is connected between the first common channel and the second common channel.

21. The fluidic device of claim 20, wherein each channel module has
an intermediate channel connected between the first common channel and the second common channel;
a first channel connected to the intermediate channel at a first position and one of the pair of input ports; and
a second channel connected to the intermediate channel at a second position and the other of the pair of input ports,
wherein the first position is between the first common channel and the second position, and the second position is between the first position and the second common channel.

22. The fluidic device of claim 21, wherein each of three actuating elements of the plurality of actuating elements are over the intermediate channel of a respective channel module at first, second and third locations in first, second and third channel portions of the intermediate channel, respectively, wherein the first channel portion is between the first common channel and the first position, the second channel portion is between the second position and the second common channel, and the third channel portion is between the first and second positions.

23. The fluidic device of claim 22, wherein the actuator head comprises an outer relief for controlling access to the at least one sensing port, an inner relief for controlling access to the at least one make-up media port, and a middle relief pocket having two ends and a gap defined therebetween.

24. The fluidic device of claim 23, wherein
when the outer relief, the inner relief, and the gap are misaligned with any channel module, all of the first and second actuating elements are pressed by the surface of the actuator head, while all of the third actuating elements are relaxed by the middle relief pocket, so that each channel module is in the run mode; and
when the outer relief, the inner relief, and the gap are aligned with the intermediate channel of a channel module, the first and second actuating elements on said channel module are relaxed by the first and second reliefs, respectively, and the third actuating element on said channel module is pressed by the gap, all of the first and second actuating elements on the other channel modules are pressed by the surface of the actuator head, while all of the third actuating elements on the other channel modules are relaxed by the middle relief pocket, so that said channel module is in the analysis mode and all of the other channel modules are in the run mode.

25. The fluidic device of claim 23, wherein a rotation of the actuator head at a predetermined angle selects which channel module is in the analysis mode.

26. The fluidic device of claim 25, wherein replacement fluid can be injected into the output line of the isolated module without disturbing the flows of the other fluidic modules.

27. The fluidic device of claim 20, wherein the fluidic network further comprises one or more additional ports for flushing the first common channel and/or the second common channel.

* * * * *